(12) United States Patent
Bachmann et al.

(10) Patent No.: US 7,767,212 B2
(45) Date of Patent: Aug. 3, 2010

(54) CAT ALLERGEN CONJUGATES AND USES THEREOF

(75) Inventors: Martin Bachmann, Seuzach (CH); Monika Bauer, Zurich (CH); Klaus Dietmeier, Zurich (CH); Nicole Schmitz, Urdorf (CH); Stephan Utzinger, Schlieren (CH)

(73) Assignee: Cytos Biotechnology AG, Zurich-Schlieren (CH)

( * ) Notice: Subject to any disclaimer, the term of this patent is extended or adjusted under 35 U.S.C. 154(b) by 44 days.

(21) Appl. No.: 11/886,577

(22) PCT Filed: Mar. 17, 2006

(86) PCT No.: PCT/EP2006/060845

§ 371 (c)(1),
(2), (4) Date: Sep. 18, 2007

(87) PCT Pub. No.: WO2006/097530

PCT Pub. Date: Sep. 21, 2006

(65) Prior Publication Data

US 2009/0175896 A1 Jul. 9, 2009

Related U.S. Application Data

(60) Provisional application No. 60/662,918, filed on Mar. 18, 2005.

(51) Int. Cl.
*A61K 39/35* (2006.01)
*A61K 39/385* (2006.01)
*C12N 7/00* (2006.01)
*C07K 19/00* (2006.01)
*C07K 17/06* (2006.01)

(52) U.S. Cl. .............. 424/275.1; 424/192.1; 424/193.1; 424/194.1; 424/196.11; 424/185.1; 435/235.1; 530/403

(58) Field of Classification Search ........................ None
See application file for complete search history.

(56) References Cited

U.S. PATENT DOCUMENTS

| | | | |
|---|---|---|---|
| 5,071,651 | A | 12/1991 | Sabara et al. |
| 5,374,426 | A | 12/1994 | Sabara et al. |
| 5,698,424 | A | 12/1997 | Mastico et al. |
| 6,054,312 | A | 4/2000 | Larocca et al. |
| 6,096,315 | A | 8/2000 | Zimmerman et al. |
| 6,120,769 | A | 9/2000 | Gefter et al. |
| 6,159,728 | A | 12/2000 | Stockley et al. |
| 6,719,978 | B2 | 4/2004 | Schiller et al. |
| 6,759,234 | B1 | 7/2004 | Gefter et al. |
| 6,759,385 | B1 | 7/2004 | Conti-Fine |
| 2002/0164342 | A1 | 11/2002 | Guyre et al. |
| 2002/0173625 | A1 | 11/2002 | Linhart et al. |
| 2002/0187158 | A1 | 12/2002 | Mahler et al. |
| 2006/0251620 | A1 | 11/2006 | Ivanova et al. |

FOREIGN PATENT DOCUMENTS

| | | |
|---|---|---|
| EP | 1 219 300 A1 | 7/2002 |
| WO | WO 92/11291 | 7/1992 |
| WO | WO 96/07428 A1 | 3/1996 |
| WO | WO 96/30523 | 10/1996 |
| WO | WO 98/15631 | 4/1998 |
| WO | WO 00/06694 A2 | 2/2000 |
| WO | WO 00/20032 A1 | 4/2000 |
| WO | WO 00/32227 * | 6/2000 |
| WO | WO 01/85208 | 11/2001 |
| WO | WO 02/40676 A2 | 5/2002 |
| WO | WO 02/056905 | 7/2002 |
| WO | WO 02/070665 A2 | 9/2002 |
| WO | WO 03/024480 | 3/2003 |
| WO | WO 03/024481 | 3/2003 |
| WO | WO 2004/007538 | 1/2004 |
| WO | WO 2004/009124 | 1/2004 |
| WO | WO 2004/039834 A2 | 5/2004 |
| WO | WO 2004/047793 A1 | 6/2004 |
| WO | WO 2004/047794 A2 | 6/2004 |
| WO | WO 2004/094639 A2 | 11/2004 |

OTHER PUBLICATIONS

Kaiser et al (Journal of Biological Chemistry 278:37730-37735, 2003).*
Vailes et al (Journal of Allergy and Clinical Immunology 110: 757-572, 2002).*
Lechner et al (Intervirology 45:212-217, 2002).*
Adhin, MR, Hirashima, A, van Duin, J, Nucleotide sequence from the ssRNA bacteriophage JP34 resolves the discrepancy between serological and biophysical classification. Virology, vol. 170(1) pp. 238-242, 1989.
Andersson, TN, Ekman, GJ, Grönlund, H, Buentke, E, Eriksson, TL, Scheynius, A, van Hage-Hamsten, M, Gafvelin, G, A novel adjuvant-allergen complex, CBP-rFel d 1, induces up-regulation of CD86 expression and enhances cytokine release by human dendritic cells in vitro. Immunology, vol. 113(2) pp. 253-259, 2004.

(Continued)

*Primary Examiner*—Mary E Mosher
(74) *Attorney, Agent, or Firm*—Sterne, Kessler, Goldstein & Fox P.L.L.C.

(57) ABSTRACT

The present invention is in the fields of medicine, public health, immunology, molecular biology and virology. The invention provides compositions comprising a virus-like particle (VLP) or a virus particle and at least one antigen, particularly at least one feline antigen, and more particularly at least one feline antigen that is a human allergen. In certain embodiments, the antigen is a Fel d1 antigen or a fragment thereof, covalently linked to the VLP. The invention also provides methods for producing the compositions. The compositions of the invention induce efficient immune responses, in particular antibody responses, in mammals, particularly humans. The compositions and methods of the invention are useful in the production of vaccines, in particular for the treatment and/or prevention of allergies to cat dander and other cat antigens and allergens.

23 Claims, 4 Drawing Sheets

OTHER PUBLICATIONS

Figure 1:
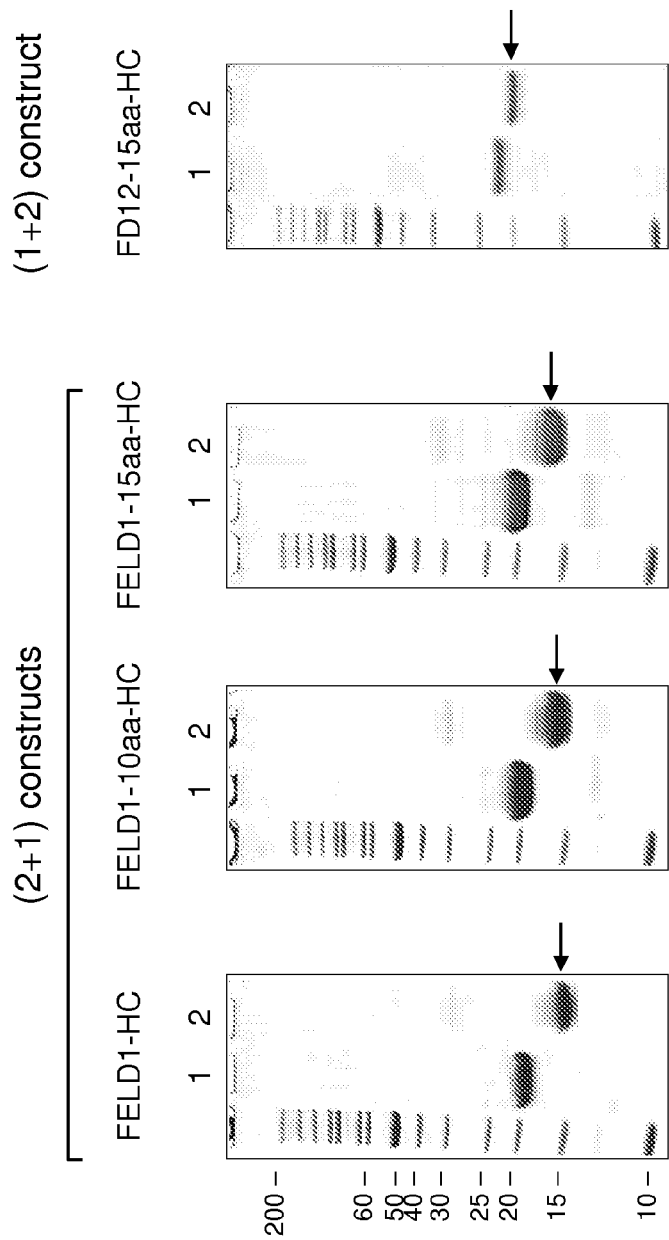

Bachmann, MF, Rohrer, UH, Kündig, TM, Bürki, K, Hengartner, H, Zinkernagel, RM, The influence of antigen organization on B cell responsiveness. Science, vol. 262(5138) pp. 1448-1451, 1993.

Batard, T, Bukovec, F, Berrouet, C, Destombes, V, Didierlaurent, A, André, C, Demonstration of a partially cryptic epitope of the major cat allergen Fel d 1: consequences for mAb-based standardization of cat extracts. J Allergy Clin Immunol, vol. 106(4) pp. 669-676, 2000.

Bond, JF, Brauer, AW, Segal, DB, Nault, AK, Rogers, BL, Kuo, MC, Native and recombinant Fel dl as probes into the relationship of allergen structure to human IgE immunoreactivity. Mol Immunol, vol. 30(16) pp. 1529-1541, 1993.

Chapman, MD, Aalberse, RC, Brown, MJ, Platts-Mills, TA, Monoclonal antibodies to the major feline allergen Fel d I. II. Single step affinity purification of Fel d I, N-terminal sequence analysis, and development of a sensitive two-site immunoassay to assess Fel d I exposure. J Immunol, vol. 140(3) pp. 812-818, 1988.

Counsell, CM, Bond, JF, Ohman, JL, Greenstein, JL, Garman, RD, Definition of the human T-cell epitopes of Fel d 1, the major allergen of the domestic cat. J Allergy Clin Immunol, vol. 98(5 Pt 1) pp. 884-894, 1996.

Cunningham, BC, Wells, JA, High-resolution epitope mapping of hGH-receptor interactions by alanine-scanning mutagenesis. Science, vol. 244(4908) pp. 1081-1085, 1989.

Duffort, OA, Carreira, J, Nitti, G, Polo, F, Lombardero, M, Studies on the biochemical structure of the major cat allergen Felis domesticus I. Mol Immunol, vol. 28(4-5) pp. 301-309, 1991.

Geysen, HM, Meloen, RH, Barteling, SJ, Use of peptide synthesis to probe viral antigens for epitopes to a resolution of a single amino acid. Proc Natl Acad Sci U S A, vol. 81(13) pp. 3998-4002, 1984.

Golmohammadi, R, Fridborg, K, Bundule, M, Valegård, K, Liljas, L, The crystal structure of bacteriophage Q beta at 3.5 A resolution. Structure, vol. 4(5) pp. 543-554, 1996.

Griffith, I, Craig, S, Pollock, J, Yu, X, Morgenstern, J, Expression and genomic structure of the genes encoding FDI, the major allergen from the domestic cat Gene, vol. 113(NA) pp. 263-268, 1992.

Grönlund, H, Bergman, T, Sandström, K, Alvelius, G, Reininger, R, Verdino, P, Hauswirth, A, Liderot, K, Valent, P, Spitzauer, S, Keller, W, Valenta, R, van Hage-Hamsten, M, Formation of disulfide bonds and homodimers of the major cat allergen Fel d 1 equivalent to the natural allergen by expression in *Escherichia coli*. J Biol Chem, vol. 278(41) pp. 40144-40151, 2003.

Hedlin, G, Graff-Lonnevig, V, Heilborn, H, Lilja, G, Norrlind, K, Pegelow, K, Sundin, B, Lowenstein, H, Immunotherapy with cat- and dog-dander extracts. V. Effects of 3 years of treatment. J Allergy Clin Immunol, vol. 87(5) pp. 955-964, 1991.

Horton, RM, Hunt, HD, Ho, SN, Pullen, JK, Pease, LR, Engineering hybrid genes without the use of restriction enzymes: gene splicing by overlap extension. Gene, vol. 77(1) pp. 61-68, 1989.

Jegerlehner, A, Maurer, P, Bessa, J, Hinton, HJ, Kopf, M, Bachmann, MF, TLR9 signaling in B cells determines class switch recombination to IgG2a. J Immunol, vol. 178(4) pp. 2415-2420, 2007.

Jegerlehner, A, Storni, T, Lipowsky, G, Schmid, M, Pumpens, P, Bachmann, MF, Regulation of IgG antibody responses by epitope density and CD21-mediated costimulation. Eur J Immunol, vol. 32(11) pp. 3305-3314, 2002.

Jegerlehner, A, Tissot, A, Lechner, F, Sebbel, P, Erdmann, I, Kündig, T, Bächi, T, Storni, T, Jennings, G, Pumpens, P, Renner, WA, Bachmann, MF, A molecular assembly system that renders antigens of choice highly repetitive for induction of protective B cell responses. Vaccine, vol. 20(25-26) pp. 3104-3112, 2002.

Jiang, XJ, Graham, DG, Wang, KW, Estes, ME, Norwalk Virus Genome Cloning and Characterization Science, vol. 250(NA) pp. 1580-1583, 1990.

Kaiser, L, Grönlund, H, Sandalova, T, Ljunggren, HG, van Hage-Hamsten, M, Achour, A, Schneider, G, The crystal structure of the major cat allergen Fel d 1, a member of the secretoglobin family. J Biol Chem, vol. 278(39) pp. 37730-37735, 2003.

Kastelein, RA, Berkhout, B, Overbeek, GP, van Duin, J, Effect of the sequences upstream from the ribosome-binding site on the yield of protein from the cloned gene for phage MS2 coat protein. Gene, vol. 23(3) pp. 245-254, 1983.

Keating, KM, Segal, DB, Craig, SJ, Nault, AK, Semensi, V, Wasserman, AS, Counsell, CM, Bond, JF, Enhanced immunoreactivity and preferential heterodimer formation of reassociated Fel d I recombinant chains. Mol Immunol, vol. 32(4) pp. 287-293, 1995.

Kozlovska, TM, Cielens, I, Dreilinna, D, Dislers, A, Baumanis, V, Ose, V, Pumpens, P, Recombinant RNA phage Q beta capsid particles synthesized and self-assembled in *Escherichia coli*. Gene, vol. 137(1) pp. 133-137, 1993.

Kozlovska, TM, Cielens, I, Vasiljeva, I, Strelnikova, A, Kazaks, A, Dislers, A, Dreilina, D, Ose, V, Gusars, I, Pumpens, P, RNA phage Q beta coat protein as a carrier for foreign epitopes. Intervirology, vol. 39(1-2) pp. 9-15, 1996.

Kozlovskaya, TK, Formation of capsid-like structures as a result of the expression of a cloned envelope protein gene from RNA-containing bacteriophage Dokl. Akad. Nauk. SSSR, vol. 287(NA) pp. 452-455, 1986.

Kristensen, AK, Schou, C, Roepstorff, P, Determination of isoforms, N-linked glycan structure and disulfide bond linkages of the major cat allergen Fel d1 by a mass spectrometric approach. Biol Chem, vol. 378(8) pp. 899-908, 1997.

Lau, S, IIIi, S, Sommerfeld, C, Niggemann, B, Bergmann, R, von Mutius, E, Wahn, U, Early exposure to house-dust mite and cat allergens and development of childhood asthma: a cohort study. Multicentre Allergy Study Group. Lancet, vol. 356(9239) pp. 1392-1397, 2000.

Lechner, F, Jegerlehner, A, Tissot, AC, Maurer, P, Sebbel, P, Renner, WA, Jennings, GT, Bachmann, MF Virus-like particles as a modular system for novel vaccines. Intervirology, vol. 45(4-6) pp. 212-217, 2002.

Leitermann, K, Ohman, JL, Cat allergen 1: Biochemical, antigenic, and allergenic properties. J Allergy Clin Immunol, vol. 74(2) pp. 147-153, 1984.

Lilja, G, Sundin, B, Graff-Lonnevig, V, Hedlin, G, Heilborn, H, Norrlind, K, Pegelow, KO, Löwenstein, H, Immunotherapy with cat- and dog-dander extracts. IV. Effects of 2 years of treatment. J Allergy Clin Immunol, vol. 83(1) pp. 37-44, 1989.

Liljas, L, Fridborg, K, Valegård, K, Bundule, M, Pumpens, P, Crystal structure of bacteriophage fr capsids at 3.5 A resolution. J Mol Biol, vol. 244(3) pp. 279-290, 1994.

Matsui, SM, Kim, JP, Greenberg, HB, Su, W, Sun, Q, Johnson, PC, DuPont, HL, Oshiro, LS, Reyes, GR, The isolation and characterization of a Norwalk virus-specific cDNA. J Clin Invest, vol. 87(4) pp. 1456-1461, 1991.

Maurer, P, Jennings, GT, Willers, J, Rohner, F, Lindman, Y, Roubicek, K, Renner, WA, Müller, P, Bachmann, MF, A therapeutic vaccine for nicotine dependence: preclinical efficacy, and Phase I safety and immunogenicity. Eur J Immunol, vol. 35(7) pp. 2031-2040, 2005.

Morgenstern, JP, Griffith, IJ, Brauer, AW, Rogers, BL, Bond, JF, Chapman, MD, Kuo, MC, Amino acid sequence of Fel dI, the major allergen of the domestic cat: protein sequence analysis and cDNA cloning. Proc Natl Acad Sci U S A, vol. 88(21) pp. 9690-9694, 1991.

Ni, CZ, White, CA, Mitchell, RS, Wickersham, J, Kodandapani, R, Peabody, DS, Ely, KR, Crystal structure of the coat protein from the GA bacteriophage: model of the unassembled dimer. Protein Sci, vol. 5(12) pp. 2485-2493, 1996.

Norman, PS, Ohman, JL, Long, AA, Creticos, PS, Gefter, MA, Shaked, Z, Wood, RA, Eggleston, PA, Hafner, KB, Rao, P, Lichtenstein, LM, Jones, NH, Nicodemus, CF, Treatment of cat allergy with T-cell reactive peptides. Am J Respir Crit Care Med, vol. 154(6 Pt 1) pp. 1623-1628, 1996.

Ohman, JL, Lowell, FC, Bloch, KJ, Allergens of mammalian origin. III. Properties of a major feline allergen. J Immunol, vol. 113(6) pp. 1668-1677, 1974.

Oldfield, WL, Larché, M, Kay, AB, Effect of T-cell peptides derived from Fel d 1 on allergic reactions and cytokine production in patients sensitive to cats: a randomised controlled trial. Lancet, vol. 360(9326) pp. 47-53, 2002.

Priano, C, Arora, R, Butke, J, Mills, DR, A complete plasmid-based complementation system for RNA coliphage Q beta: three proteins of bacteriophages Q beta (group III) and SP (group IV) can be interchanged. J Mol Biol, vol. 249(2) pp. 283-297, 1995.

Pushko, P, Kozlovskaya, T, Sominskaya, I, Brede, A, Stankevica, E, Ose, V, Pumpens, P, Grens, E, Analysis of RNA phage fr coat protein assembly by insertion, deletion and substitution mutagenesis. Protein Eng, vol. 6(8) pp. 883-891, 1993.

Schmitz, N, Dietmeier, K, Bauer, M, Maudrich, M, Utzinger, S, Muntwiler, S, Saudan, P, Bachmann, MF, Displaying Fel d1 on virus-like particles prevents reactogenicity despite greatly enhanced immunogenicity: a novel therapy for cat allergy. J Exp Med, 2009, 206:1941-1955.

Seppälä, U, Hägglund, P, Wurtzen, PA, Ipsen, H, Thorsted, P, Lenhard, T, Roepstorff, P, Spangfort, MD, Molecular characterization of major cat allergen Fel d 1: expression of heterodimer by use of a baculovirus expression system. J Biol Chem, vol. 280(5) pp. 3208-3216, 2005.

Slunt, JB, Rogers, BL, Chapman, MD, IgE antibodies to recombinant forms of Fel d I: dichotomy between fluid-phase and solid-phase binding studies. J Allergy Clin Immunol, vol. 95(6) pp. 1221-1228, 1995.

Spohn, G, Schwarz, K, Maurer, P, Illges, H, Rajasekaran, N, Choi, Y, Jennings, GT, Bachmann, MF, Protection against osteoporosis by active immunization with TRANCE/RANKL displayed on virus-like particles. J Immunol, vol. 175(9) pp. 6211-6218, 2005.

Tars, K, Bundule, M, Fridborg, K, Liljas, L, The crystal structure of bacteriophage GA and a comparison of bacteriophages belonging to the major groups of *Escherichia coli* leviviruses. J Mol Biol, vol. 271(5) pp. 759-773, 1997.

Tissot, AC, Maurer, P, Nussberger, J, Sabat, R, Pfister, T, Ignatenko, S, Volk, HD, Stocker, H, Müller, P, Jennings, GT, Wagner, F, Bachmann, MF, Effect of immunisation against angiotensin II with CYT006-AngQb on ambulatory blood pressure: a double-blind, randomised, placebo-controlled phase IIa study. Lancet, vol. 371(9615) pp. 821-827, 2008.

Twomey, T, Newman, J, Burrage, T, Piatti, P, Lubroth, J, Brown, F, Structure and immunogenicity of experimental foot-and-mouth disease and poliomyelitis vaccines. Vaccine, vol. 13(16) pp. 1603-1610, 1995.

Ulrich, R, Nassal, M, Meisel, H, Krüger, DH, Core particles of hepatitis B virus as carrier for foreign epitopes. Adv Virus Res, vol. 50( ) pp. 141-182, 1998.

Vailes, LD, Li, Y, Bao, Y, DeGroot, H, Aalberse, RC, Chapman, MD, Fine specificity of B-cell epitopes on Felis domesticus allergen I (Fel d I): effect of reduction and alkylation or deglycosylation on Fel d I structure and antibody binding. J Allergy Clin Immunol, vol. 93(1 Pt 1) pp. 22-33, 1994.

Vailes, LD, Sun, AW, Ichikawa, K, Wu, Z, Sulahian, TH, Chapman, MD, Guyre, PM, High-level expression of immunoreactive recombinant cat allergen (Fel d 1): Targeting to antigen-presenting cells. J Allergy Clin Immunol, vol. 110(5) pp. 757-762, 2002.

van Milligen, FJ, van 't Hof, W, van den Berg, M, Aalberse, RC, IgE epitopes on the cat (Felis domesticus) major allergen Fel d I: a study with overlapping synthetic peptides. J Allergy Clin Immunol, vol. 93(1 Pt 1) pp. 34-43, 1994.

van Ree, R, van Leeuwen, WA, Bulder, I, Bond, J, Aalberse, RC, Purified natural and recombinant Fel d 1 and cat albumin in in vitro diagnostics for cat allergy. J Allergy Clin Immunol, vol. 104(6) pp. 1223-1230, 1999.

van 't Hof, W, van Milligen, FJ, van den Berg, M, Lombardero, M, Chapman, MD, Aalberse, RC, Epitope mapping of the cat (Felis domesticus) major allergen Fel d I by overlapping synthetic peptides and monoclonal antibodies against native and denatured Fel d I. Allergy, vol. 48(4) pp. 255-263, 1993.

Warnes, A, Fooks, AR, Dowsett, AB, Wilkinson, GW, Stephenson, JR, Expression of the measles virus nucleoprotein gene in *Escherichia coli* and assembly of nucleocapsid-like structures. Gene, vol. 160(2) pp. 173-178, 1995.

\* cited by examiner

CAT ALLERGEN CONJUGATES AND USES THEREOF

CROSS REFERENCE TO RELATED APPLICATIONS

The present invention is a U.S. National Phase filing under 35 U.S.C. §371 of PCT/EP2006/060845, filed Mar. 17, 2006, which was published in the English language as WO 2006/097530 A2 on Sep. 21, 2006, and which claims benefit of U.S. Provisional Patent Application No. 60/662,918, filed Mar. 18, 2005, the disclosures of each of which are incorporated herein by reference in their entireties.

BACKGROUND OF THE INVENTION

1. Field of the Invention

The present invention is in the fields of medicine, public health, immunology, molecular biology and virology. The invention provides compositions comprising a virus-like particle (VLP) or a virus particle and at least one antigen, particularly at least one feline antigen, and more particularly at least one feline antigen that is a human allergen. In certain embodiments, the antigen is a Fel d1 antigen or a fragment thereof, covalently linked to the VLP. The invention also provides methods for producing the compositions. The compositions of the invention induce efficient immune responses, in particular antibody responses, in mammals, particularly humans. The compositions and methods of the invention are useful in the production of vaccines, in particular for the treatment and/or prevention of allergies to cat dander and other cat antigens and allergens.

2. Related Art

The domestic cat (*Felis domesticus*) is an important source of indoor allergens (Lau, S., et al. (2000) Lancet 356, 1392-1397). Indeed, cats are found in about 25% of households in Western countries and allergy to cats is found in a large part of the population. The severity of symptoms range from relatively mild rhinitis and conjunctivitis to potentially life-threatening asthmatic exacerbation.

Although patients are occasionally sensitised to several different molecules in cat dander and pelts, the major allergen is Fel d 1 (i.e. *Felis domesticus* allergen 1; formerly Cat 1, i.e. Cat allergen 1). The importance of this allergen has been emphasised in numerous studies. In fact more than 80% of cat allergic patients exhibit IgE antibodies to this potent allergen (van Ree, R., et al. (1999) J. Allergy Clin Immunol 104, 1223-1230).

Fel d1 is a 35-39 kDa acidic glycoprotein containing 10-20% N-linked carbohydrates and is found in the pelt, saliva and lachrymal glands of cats. It is formed by two non-covalently linked heterodimers. Each heterodimer consists of one 70 residue peptide (known as "chain 1") and one 78, 85, 90 or 92 residue peptide (known as "chain 2") which are encoded by separate genes (see Duffort, O. A., et al. (1991) Mol Immunol 28, 301-309; Morgenstern, J. P., et al; (1991) Proc Natl Acad Sci USA 88, 9690-9694 and Griffith, I. J., et al. (1992) Gene 113, 263-268).

Treatment of cat allergic patients is currently effected by desensitization therapy involving repeated injections with increasing dosages of either a crude cat dander extract or short peptides derived from Fel d1. Lilja et al and Hedlin et al have disclosed a desensitization program in the course of which crude cat dander extracts have been given to cat allergic patients (Lilja, Q, et al. (1989) J Allergy Clin Immunol 83, 37-44 and Hedlin, et al. (1991) J Allergy Clin Immunol 87, 955-964). This program took at least two to three years and the patients after three year treatment still had systemic symptoms. Using short peptides derived from Fel d1 for desensitization resulted in non-significant difference between the peptide group and the placebo group (Oldfield, W. L., et al. (2002) Lancet 360, 47-53). Efficacy was only seen when large amount (750 µg) of the short peptide was given to patients (Norman, P. S., et al. (1996) Am J Respir Crit Care Med 154, 1623-1628).

Allergic side effects, such as late asthmatic reactions, have been reported in both crude cat dander extract treatment and in short peptide treatment. Therefore, anaphylactic shock due to the injected allergen is of great safety concern for any desensitization program. Avoidance of such effect by reducing the injected amount of allergen, however, either reduces the efficacy of the treatment or prolongs the treatment. Thus, there is a great need in the field of cat-allergy treatment for alternative desensitization regimes, and hereby in particular for desensitization regimes that are able to reduce allergic symptoms, but do not trigger allergic side reaction.

SUMMARY OF THE INVENTION

We have, now, surprisingly found that the inventive compositions and vaccines, respectively, comprising at least one Fel d1 antigen or fragment thereof of the invention, are not only capable of inducing immune responses against Fel d1, and hereby in particular antibody responses, but are, furthermore, capable of desensitizing a patient suffering from cat allergy, and hereby in particular, within a short period of time, indicating the high efficacy of the inventive compositions and vaccines, respectively. In addition, we have surprisingly found that Fel d1 of the invention, when covalently linked to the VLP in accordance with the invention, has dramatically reduced anaphylactic activity as compared to Fel d1 of the invention not covalently linked to VLP while maintaining a high degree of antigenecity and immunogenecity. This is of great advantage over prior art cat allergy treatments because the inventive compositions and vaccines, respectively, dramatically reduce the risk of causing anaphylactic shock in animals and humans to be immunized. Furthermore, the inventive compositions and vaccines, respectively, allow the antigen to be given in much higher dose compared with prior art cat allergy treatments, which may in turn improve the efficacy and/or shorten the whole desensitization program. Thus, the inventive compositions and vaccines, respectively, induce potent anti-Fel d1 immune responses but do not trigger an allergic reaction.

Thus, in the first aspect, the present invention provides a composition which comprises (a) a core particle with at least one first attachment site, wherein said core particle is a virus-like particle (VLP) or a virus particle; and (b) at least one antigen with at least one second attachment site, wherein said at least one antigen is Fel d1 protein or a Fel d1 fragment, and wherein (a) and (b) are covalently linked through said at least one first and said at least one second attachment site, preferably to form an ordered and repetitive antigen array.

In another aspect, the present invention provides a vaccine composition. Furthermore, the present invention provides a method to administering the vaccine composition to a human or a non-human mammal, such as dog, which is allergic to cat, preferably to cat Fel d1. In one preferred embodiment, the vaccine composition further comprises at least one adjuvant. The inventive vaccine composition is, however, capable of inducing strong immune response, in particular antibody response, without the presence of at least one adjuvant. Thus, in one preferred embodiment, the vaccine is devoid of an adjuvant. The avoidance of using adjuvant may reduce a possible occurrence of side effects relating to the using of adjuvants.

In one preferred embodiment, the VLP comprised by the composition and the vaccine composition, respectively, is recombinantly produced in a host and the VLP is essentially free of host RNA, preferably free of host nucleic acids. It is advantageous to reduce, or preferably to eliminate, the amount of host, preferably free of host nucleic acids, to avoid unwanted T cell responses as well as other unwanted side effects, such as fever.

In one preferred embodiment, the composition of the invention further comprises at least one immunostimulatory substance, preferably at least one immunostimulatory nucleic acid. In one further preferred embodiment, the immunostimulatory nucleic acid is packaged inside the VLP of the invention. The inclusion of immunostimulatory substances, preferably immunostimulatory nucleic acids, into the composition of the invention may drives the immune responses towards Th1 responses and thereby suppressing the Th2 responses and hence suppressing the production of IgE.

In one aspect, the present invention provides a method of treating cat allergy by administering the inventive composition or vaccine, respectively, into a cat allergic object, preferably human.

In a further aspect, the present invention provides a pharmaceutical composition comprising the inventive composition and an acceptable pharmaceutical carrier.

In again a further aspect, the present invention provides for a method of producing the composition of the invention comprising (a) core particle with at least one first attachment site, wherein said core particle is a virus-like particle (VLP) or a virus particle; (b) providing at least one antigen with at least one second attachment site, wherein said antigen is a Fel d1 protein or a Fel d1 fragment; and (c) combining said core particle and said at least one antigen to produce said composition, wherein said at least one antigen and said core particle are linked through said at least one first and said at least one second attachment sites.

In one aspect, the invention provides a Fel d1 fusion protein comprising chain 1 of Fel d1 and chain 2 of Fel d1 fused via an amino acid spacer, which links the N-terminus of one chain with the C-terminus of another chain, wherein said amino acid spacer consists of an amino acid sequence having 10-30 amino acid residues, and wherein said fusion protein is produced in *E. coli* or wherein said fusion protein is not glycosylated.

BRIEF DESCRIPTION OF THE FIGURES

FIG. 1 shows the Coomassie stained purified and renatured Fel d1 fusion proteins on SDS-PAGE non-reducing gel. Samples in lane 1 had DTT as reducing agent. Samples in lane 2 had no DTT.

FIG. 2 shows the degranulation of basophils by either the Fel d1 fusion proteins alone or by the Fel d1 fusion proteins coupled to Qβ. X-axis represents the concentration of the corresponding Fel d1 protein. Y-axis represents the percentage of basophiles which have been degranulated.

FIG. 3 shows the skin prick test results of a cat allergic volunteer who received Qβ-FELD1 on day 0, 7 and 14 and the tests were also carried out on day of 0, 14 and 21.

FIG. 4A shows the nasal dose escalation score and FIG. 4B shows nasal overall score of a cat allergic volunteer who received Qβ-FELD 1 on day 0, 7 and 14 and the tests were carried out on day of 0, 14 and 21.

DETAILED DESCRIPTION OF THE INVENTION

Unless defined otherwise, all technical and scientific terms used herein have the same meanings as commonly understood by one of ordinary skill in the art to which this invention belongs.

Adjuvant: The term "adjuvant" as used herein refers to non-specific stimulators of the immune response or substances that allow generation of a depot in the host which when combined with the vaccine and pharmaceutical composition, respectively, of the present invention may provide for an even more enhanced immune response. A variety of adjuvants can be used. Examples include complete and incomplete Freund's adjuvant, aluminum hydroxide and modified muramyldipeptide. Further adjuvants are mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette Guerin) and *Corynebacterium parvum*. Such adjuvants are also well known in the art. Further adjuvants that can be administered with the compositions of the invention include, but are not limited to, Monophosphoryl lipid immunomodulator, AdjuVax 100a, QS-21, QS-18, CRL1005, Aluminum salts (Alum), MF-59, OM-174, OM-197, OM-294, and Virosomal adjuvant technology. The adjuvants can also comprise a mixture of these substances. VLP has been generally described as an adjuvant. However, the term "adjuvant", as used within the context of this application, refers to an adjuvant not being the VLP used for the inventive compositions, rather in addition to said VLP.

Antigen: As used herein, the term "antigen" refers to a molecule capable of being bound by an antibody or a T cell receptor (TCR) if presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

Antigenic site: The term "antigenic site" and the term "antigenic epitope", which are used herein interchangeably, refer to continuous or discontinuous portions of a polypeptide, which can be bound immunospecifically by an antibody or by a T-cell receptor within the context of an MHC molecule. Immunospecific binding excludes non-specific binding but does not necessarily exclude cross-reactivity. Antigenic site typically comprise 5-10 amino acids in a spatial conformation which is unique to the antigenic site.

Associated: The term "associated" (or its noun association) as used herein refers to all possible ways, preferably chemical interactions, by which two molecules are joined together. Chemical interactions include covalent and non-covalent interactions. Typical examples for non-covalent interactions are ionic interactions, hydrophobic interactions or hydrogen bonds, whereas covalent interactions are based, by way of example, on covalent bonds such as ester, ether, phosphoester, amide, peptide, carbon-phosphorus bonds, carbon-sulfur bonds such as thioether, or imide bonds.

Attachment Site, First: As used herein, the phrase "first attachment site" refers to an element which is naturally occurring with the VLP or which is artificially added to the VLP, and to which the second attachment site may be linked. The first attachment site may be a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a chemically reactive group such as an amino group, a carboxyl group, a sulfhydryl group, a hydroxyl group, a guanidinyl group, histidinyl group, or a combination thereof. A preferred embodiment of a chemically reactive group being the first attachment site is the amino group of an amino acid such as lysine. The first attachment site is located, typically on the surface, and preferably on the outer surface of the VLP. Multiple first attachment sites are present on the surface, preferably on the outer surface of virus-like particle, typically in a repetitive configuration. In a preferred embodiment the first attachment site is associated with the VLP, through at least one covalent bond, preferably through at least one peptide bond. In a further preferred embodiment the first attachment site is naturally occurring with the VLP. Alternatively, in a preferred embodiment the first attachment site is artificially added to the VLP.

Attachment Site, Second: As used herein, the phrase "second attachment site" refers to an element which is naturally occurring with or which is artificially added to Fel d1 of the invention and to which the first attachment site may be linked. The second attachment site of Fel d1 of the invention may be a protein, a polypeptide, a peptide, an amino acid, a sugar, a polynucleotide, a natural or synthetic polymer, a secondary metabolite or compound (biotin, fluorescein, retinol, digoxigenin, metal ions, phenylmethylsulfonylfluoride), or a chemically reactive group such as an amino group, a carboxyl group, a sulfhydryl group, a hydroxyl group, a guanidinyl group, histidinyl group, or a combination thereof. A preferred embodiment of a chemically reactive group being the second attachment site is the sulfhydryl group, preferably of an amino acid cysteine. The terms "Fel d1 of the invention with at least one second attachment site" refers, therefore, to a construct comprising the Fel d1 of the invention and at least one second attachment site. However, in particular for a second attachment site, which is not naturally occurring within the Fel d1 of the invention, such a construct typically and preferably further comprises a "linker". In another preferred embodiment the second attachment site is associated with the Fel d1 of the invention through at least one covalent bond, preferably through at least one peptide bond. In a further embodiment, the second attachment site is naturally occurring within the Fel d1 of the invention. In another further preferred embodiment, the second attachment site is artificially added to the Fel d1 of the invention through a linker, wherein said linker comprises or alternatively consists of a cysteine. Preferably the linker is fused to the Fel d1 of the invention by a peptide bond.

Coat protein: The term "coat protein" and the interchangeably used term "capsid protein" within this application, refers to a viral protein, preferably a subunit of a natural capsid of a virus, preferably of a RNA-phage, which is capable of being incorporated into a virus capsid or a VLP.

Fel d1 of the invention: The term "Fel d1 of the invention", as used herein, refers to at least one Fel d1 protein or at least one Fel d1 fragment.

Chain 1 of Fel d1: The term "chain 1 of Fel d1", as used herein, refers to a polypeptide comprising or alternatively consisting of an amino acid sequence as of SEQ ID NO:22 or a homologous sequence thereof. The term "homologous sequence of SEQ ID NO:22", as used herein, refers to a polypeptide that has an identity to SEQ ID NO:22 which is greater than 70%, preferably greater than 80%, more preferably greater than 90%, and even more preferably greater than 95%. The term "chain 1 of Fel d1", as used herein, should also refer to a polypeptide encompassing at least one post-translational modification, including but not limited to at least one glycosylation, of chain 1 of Fel d1, as defined herein. Preferably the chain 1 of Fel d1, as defined herein, consists of at most 130, even more preferably at most 100 amino acids in total.

Chain 2 of Fel d1: The term "chain 2 of Fel d1", as used herein, refers to a polypeptide comprising or alternatively consisting of an amino acid sequence as of SEQ ID NO: 23, SEQ ID NO: 25 or SEQ ID NO: 26, or a homologous sequence thereof. The term "homologous sequence of SEQ ID NO: 23, SEQ ID NO: 25 or SEQ ID NO: 26, as used herein, refers to a polypeptide that has an identity to SEQ ID NO: 23, SEQ ID NO: 25 or SEQ ID NO: 26 which is greater than 70%, preferably greater than 80%, more preferably greater than 90%, and even more preferably greater than 95%. The term "chain 2 of Fel d1", as used herein, should also refer to a polypeptide encompassing at least one post-translational modification, including but not limited to at least one glycosylation, of chain 2 of Fel d1, as defined herein Preferably the chain 2 of Fel d1, as defined herein, consists of at most 150, even more preferably at most 130, still more preferably at most 100 amino acids in total.

Fel d1 protein: The term "Fel d1 protein", as used herein, refers to a protein comprising or alternatively consisting of chain 1 of Fel d1 and chain 2 of Fel d1. Preferably chain 1 of Fel d1 and chain 2 of Fel d1 are linked covalently. In one preferred embodiment, the chain 1 of Fel d1 and chain 2 of Fel d1 are linked via at least one disulfide bond. In another preferred embodiment, the chain 1 and chain 2 are fused either directly or via a spacer, in which case said Fel d1 protein further comprises or alternatively consists of a spacer. Preferably the Fel d1 protein, as defined herein, consists of at most 300, even more preferably at most 200 amino acids in total. Typically and preferably, Fel d1 protein, according to the invention, is capable of inducing in vivo the production of antibody specifically binding to either the naturally occurring Fel d1 or the recombinant Fel d1 as produced according to EXAMPLE 5 of the present invention.

Fel d1 fragment: The term "Fel d1 fragment" as used herein, refers to a polypeptide comprising or alternatively consisting of, at least one antigenic site of Fel d1. Typically and preferably, the term "Fel d1 fragment" as used herein, refers to a polypeptide comprising or alternatively consisting of at least two antigenic sites of Fel d1. Preferably the antigenic sites are covalently linked, further preferably the antigenic sites are linked by at least one peptide bond, in which case a spacer between the antigenic sites may be needed. Preferably the at least two antigenic sites derive both from the chain 1 of Fel d1 and from the chain 2 of Fel d1. Preferably the Fel d1 fragment, as defined herein, consists of at most 130, even more preferably at most 100, still more preferably 60 amino acids in total. Typically and preferably, the Fel d1 fragment is capable of inducing in vivo the production of antibody specifically binding to either the naturally occurring Fel d1 or the recombinant Fel d1 as produced according to EXAMPLE 5 of the present invention.

Linked: The term "linked" (or its noun: linkage) as used herein, refers to all possible ways, preferably chemical interactions, by which the at least one first attachment site and the at least one second attachment site are joined together.

Chemical interactions include covalent and non-covalent interactions. Typical examples for non-covalent interactions are ionic interactions, hydrophobic interactions or hydrogen bonds, whereas covalent interactions are based, by way of example, on covalent bonds such as ester, ether, phosphoester, amide, peptide, carbon-phosphorus bonds, carbon-sulfur bonds such as thioether, or imide bonds. In certain preferred embodiments the first attachment site and the second attachment site are linked through at least one covalent bond, preferably through at least one non-peptide bond, and even more preferably through exclusively non-peptide bond(s). The term "linked" as used herein, however, shall not only encompass a direct linkage of the at least one first attachment site and the at least one second attachment site but also, alternatively and preferably, an indirect linkage of the at least one first attachment site and the at least one second attachment site through intermediate molecule(s), and hereby typically and preferably by using at least one, preferably one, heterobifunctional cross-linker.

Linker: A "linker", as used herein, either associates the second attachment site with Fel d1 of the invention or already comprises, essentially consists of, or consists of the second attachment site. Preferably, a "linker", as used herein, already comprises the second attachment site, typically and preferably—but not necessarily—as one amino acid residue, preferably as a cysteine residue. A "linker" as used herein is also termed "amino acid linker", in particular when a linker according to the invention contains at least one amino acid residue. Thus, the terms "linker" and "amino acid linker" are interchangeably used herein. However, this does not imply that such a linker consists exclusively of amino acid residues, even if a linker consisting of amino acid residues is a preferred embodiment of the present invention. The amino acid residues of the linker are, preferably, composed of naturally occurring amino acids or unnatural amino acids known in the art, all-L or all-D or mixtures thereof. Further preferred embodiments of a linker in accordance with this invention are molecules comprising a sulfhydryl group or a cysteine residue and such molecules are, therefore, also encompassed within this invention. Further linkers useful for the present invention are molecules comprising a C1-C6 alkyl-, a cycloalkyl such as a cyclopentyl or cyclohexyl, a cycloalkenyl, aryl or heteroaryl moiety. Moreover, linkers comprising preferably a C1-C6 alkyl-, cycloalkyl-(C5, C6), aryl- or heteroaryl-moiety and additional amino acid(s) can also be used as linkers for the present invention and shall be encompassed within the scope of the invention. Association of the linker with the Fel d1 of the invention is preferably by way of at least one covalent bond, more preferably by way of at least one peptide bond.

Ordered and repetitive antigen array: As used herein, the term "ordered and repetitive antigen array" generally refers to a repeating pattern of antigen or, characterized by a typically and preferably high order of uniformity in spacial arrangement of the antigens with respect to virus-like particle, respectively. In one embodiment of the invention, the repeating pattern may be a geometric pattern. Certain embodiments of the invention, such as antigens coupled to the VLP of RNA phages, are typical and preferred examples of suitable ordered and repetitive antigen arrays which, moreover, possess strictly repetitive paracrystalline orders of antigens, preferably with spacings of 1 to 30 nanometers, preferably 2 to 15 nanometers, even more preferably 2 to 10 nanometers, even again more preferably 2 to 8 nanometers, and further more preferably 1.6 to 7 nanometers.

Packaged: The term "packaged" as used herein refers to the state of a polyanionic macromolecule or immunostimulatory substances in relation to the VLP. The term "packaged" as used herein includes binding that may be covalent, e.g., by chemically coupling, or non-covalent, e.g., ionic interactions, hydrophobic interactions, hydrogen bonds, etc. The term also includes the enclosement, or partial enclosement, of a polyanionic macromolecule. Thus, the polyanionic macromolecule or immunostimulatory substances can be enclosed by the VLP without the existence of an actual binding, in particular of a covalent binding. In preferred embodiments, the at least one polyanionic macromolecule or immunostimulatory substances is packaged inside the VLP, most preferably in a non-covalent manner.

Spacer: The term "spacer", as well as its equivalently used term "amino acid spacer", as used herein, refers to a stretch of amino acid sequence, which is not more than 30 amino acids, and which links the N-terminus of one chain with the C-terminus of another chain of Fel d1.

Virus particle: The term "virus particle" as used herein refers to the morphological form of a virus. In some virus types it comprises a genome surrounded by a protein capsid; others have additional structures (e.g., envelopes, tails, etc.).

Virus-like particle (VLP), as used herein, refers to a non-replicative or non-infectious, preferably a non-replicative and non-infectious virus particle, or refers to a non-replicative or non-infectious, preferably a non-replicative and non-infectious structure resembling a virus particle, preferably a capsid of a virus. The term "non-replicative", as used herein, refers to being incapable of replicating the genome comprised by the VLP. The term "non-infectious", as used herein, refers to being incapable of entering the host cell. Preferably a virus-like particle in accordance with the invention is non-replicative and/or non-infectious since it lacks all or part of the viral genome or genome function. In one embodiment, a virus like particle is a virus particle, in which the viral genome has been physically or chemically inactivated. Typically and more preferably a virus-like particle lacks all or part of the replicative and infectious components of the viral genome. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, preferably RNA-phage. The terms "viral capsid" or "capsid", refer to a macromolecular assembly composed of viral protein subunits. Typically, there are 60, 120, 180, 240, 300, 360 and more than 360 viral protein subunits. Typically and preferably, the interactions of these subunits lead to the formation of viral capsid or viral-capsid like structure with an inherent repetitive organization, wherein said structure is, typically, spherical or tubular. For example, the capsids of RNA-phages or HBcAgs have a spherical form of icosahedral symmetry. The term "capsid-like structure" as used herein, refers to a macromolecular assembly composed of viral protein subunits resembling the capsid morphology in the above defined sense but deviating from the typical symmetrical assembly while maintaining a sufficient degree of order and repetitiveness.

One common feature of virus particle and virus-like particle is its highly ordered and repetitive arrangement of its subunits.

Virus-like particle of a RNA phage: As used herein, the term "virus-like particle of a RNA phage" refers to a virus-like particle comprising, or preferably consisting essentially of or consisting of coat proteins, mutants or fragments thereof, of a RNA phage. In addition, virus-like particle of a RNA phage resembling the structure of a RNA phage, being non replicative and/or non-infectious, and lacking at least the gene or genes encoding for the replication machinery of the RNA phage, and typically also lacking the gene or genes encoding the protein or proteins responsible for viral attachment to or entry into the host. This definition should, however, also encompass virus-like particles of RNA phages, in which the aforementioned gene or genes are still present but inactive, and, therefore, also leading to non-replicative and/or non-infectious virus-like particles of a RNA phage. Preferred VLPs derived from RNA-phages exhibit icosahedral symmetry and consist of 180 subunits. Within this present disclosure the term "subunit" and "monomer" are interexchangeably and equivalently used within this context. In this application, the term "RNA-phage" and the term "RNA-bacteriophage" are interchangeably used. Preferred methods to render a virus-like particle of a RNA phage non replicative and/or non-infectious is by physical, chemical inactivation, such as UV irradiation, formaldehyde treatment, typically and preferably by genetic manipulation.

One, a, or an: when the terms "one", "a", or "an" are used in this disclosure, they mean "at least one" or "one or more" unless otherwise indicated.

The amino acid sequence identity of polypeptides can be determined conventionally using known computer programs such as the Bestfit program. When using Bestfit or any other sequence alignment program, preferably using Bestfit, to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed. This aforementioned method in determining the percentage of identity between polypeptides is applicable to all proteins, polypeptides or a fragment thereof disclosed in this invention.

Within this application, antibodies are defined to be specifically binding if they bind to the antigen with a binding affinity (Ka) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The affinity of an antibody can be readily determined by one of ordinary skill in the art (for example, by Scatchard analysis.)

This invention provides compositions of the invention comprising: (a) a core particle with at least one first attachment site, wherein said core particle is a virus-like particle (VLP) or a virus particle; and (b) at least one antigen with at least one second attachment site, wherein the at least one antigen is a Fel d1 protein or a Fel d1 fragment and wherein (a) and (b) are covalently linked through the at least one first and the at least one second attachment site. Preferably, a Fel d1 protein or a Fel d1 fragment is linked to the core particle, so as to form an ordered and repetitive antigen-VLP array. In preferred embodiments of the invention, at least 20, preferably at least 30, more preferably at least 60, again more preferably at least 120 and further more preferably at least 180 a Fel d1 protein or a Fel d1 fragment are linked to the core particle.

Any virus known in the art having an ordered and repetitive structure may be selected as a VLP or a virus particle of the invention. Illustrative DNA or RNA viruses, the coat or capsid protein of which can be used for the preparation of VLPs have been disclosed in WO 2004/009124 on page 25, line 10-21, on page 26, line 11-28, and on page 28, line 4 to page 31, line 4. These disclosures are incorporated herein by way of reference.

Virus or virus-like particle can be produced and purified from virus-infected cell culture. The resulting virus or virus-like particle for vaccine purpose should be preferably non-replicative or non-infectious, more preferably non-replicative and non-infectious. UV irradiation, chemical treatment, such as with formaldehyde or chloroform, are the general methods known to skilled person in the art to inactivate virus.

In one preferred embodiment, the core particle is a virus particle, and wherein preferably said virus particle is a virus particle of a bacteriophage, and wherein further preferably said bacteriophage is a RNA phage, and wherein even further preferably said RNA-phage is a RNA phage selected from Qβ, fr, GA or AP205.

In one preferred embodiment, the core particle is a VLP. In a further preferred embodiment, the VLP is a recombinant VLP. Almost all commonly known viruses have been sequenced and are readily available to the public. The gene encoding the coat protein can be easily identified by a skilled artisan. The preparation of VLPs by recombinantly expressing the coat protein in a host is within the common knowledge of a skilled artisan.

In one preferred embodiment, the virus-like particle comprises, or alternatively consists of, recombinant proteins, mutants or fragments thereof, of a virus selected form the group consisting of: a) RNA phages; b) bacteriophages; c) Hepatitis B virus, preferably its capsid protein (Ulrich, et al., Virus Res. 50:141-182 (1998)) or its surface protein (WO 92/11291); d) measles virus (Warnes, et al., Gene 160:173-178 (1995)); e) Sindbis virus; f) rotavirus (U.S. Pat. No. 5,071,651 and U.S. Pat. No. 5,374,426); g) foot-and-mouth-disease virus (Twomey, et al., Vaccine 13:1603 1610, (1995)); h) Norwalk virus (Jiang, X., et al., Science 250:1580 1583 (1990); Matsui, S. M., et al., J. Clin. Invest 87:1456 1461 (1991)); i) Alphavirus; j) retrovirus, preferably its GAG protein (WO 96/30523); k) retrotransposon Ty, preferably the protein p1; 1) human Papilloma virus (WO 98/15631); m) Polyoma virus; n) Tobacco mosaic virus; and o) Flock House Virus.

In one preferred embodiment, the VLP comprises, or consists of, more than one amino acid sequence, preferably two amino acid sequences, of the recombinant proteins, mutants or fragments thereof. VLP comprises or consists of more than one amino acid sequence is referred, in this application, as mosaic VLP.

The term "fragment of a recombinant protein" or the term "fragment of a coat protein", as used herein, is defined as a polypeptide, which is of at least 70%, preferably at least 80%, more preferably at least 90%, even more preferably at least 95% the length of the wild-type recombinant protein, or coat protein, respectively and which preferably retains the capability of forming VLP. Preferably the fragment is obtained by at least one internal deletion, at least one truncation or at least one combination thereof. The term "fragment of a recombinant protein" or "fragment of a coat protein" shall further encompass polypeptide, which has at least 80%, preferably 90%, even more preferably 95% amino acid sequence identity with the "fragment of a recombinant protein" or "fragment of a coat protein", respectively, as defined above and which is preferably capable of assembling into a virus-like particle.

The term "mutant recombinant protein" or the term "mutant of a recombinant protein" as interchangeably used in this invention, or the term "mutant coat protein" or the term "mutant of a coat protein", as interchangeably used in this invention, refers to a polypeptide having an amino acid sequence derived from the wild type recombinant protein, or coat protein, respectively, wherein the amino acid sequence is at least 80%, preferably at least 85%, 90%, 95%, 97%, or 99% identical to the wild type sequence and preferably retains the ability to assemble into a VLP.

In one preferred embodiment, the virus-like particle of the invention is of Hepatitis B virus. The preparation of Hepatitis B virus-like particles have been disclosed, inter alia, in WO 00/32227, WO 01/85208 and in WO 02/056905. All three documents are explicitly incorporated herein by way of reference. Other variants of HBcAg suitable for use in the practice of the present invention have been disclosed in page 34-39 WO 02/056905.

In one further preferred embodiments of the invention, a lysine residue is introduced into the HBcAg polypeptide, to mediate the linking of Fel d1 of the invention to the VLP of HBcAg. In preferred embodiments, VLPs and compositions of the invention are prepared using a HBcAg comprising, or alternatively consisting of, amino acids 1-144, or 1-149, 1-185 of SEQ ID NO:20, which is modified so that the amino acids at positions 79 and 80 are replaced with a peptide having the amino acid sequence of Gly-Gly-Lys-Gly-Gly. This modification changes the SEQ ID NO:20 to SEQ ID NO:21. In further preferred embodiments, the cysteine residues at positions 48 and 110 of SEQ ID NO:21, or its corresponding fragments, preferably 1-144 or 1-149, are mutated to serine. The invention further includes compositions comprising Hepatitis B core protein mutants having above noted corresponding amino acid alterations. The invention further includes compositions and vaccines, respectively, comprising HBcAg polypeptides which comprise, or alternatively consist of, amino acid sequences which are at least 80%, 85%, 90%, 95%, 97% or 99% identical to SEQ ID NO:21.

In one preferred embodiment of the invention, the virus-like particle of the invention comprises, consists essentially of, or alternatively consists of, recombinant coat proteins, mutants or fragments thereof, of a RNA-phage. Preferably, the RNA-phage is selected from the group consisting of a) bacteriophage Qβ; b) bacteriophage R17; c) bacteriophage fr; d) bacteriophage GA; e) bacteriophage SP; f) bacteriophage MS2; g) bacteriophage M11; h) bacteriophage MX1; i) bacteriophage NL95; k) bacteriophage f2; 1) bacteriophage PP7 and m) bacteriophage AP205.

In one preferred embodiment of the invention, the composition comprises coat protein, mutants or fragments thereof, of RNA phages, wherein the coat protein has amino acid sequence selected from the group consisting of: (a) SEQ ID NO:1; referring to Qβ CP; (b) a mixture of SEQ ID NO:1 and SEQ ID NO:2 (referring to Qβ A1 protein); (c) SEQ ID NO:3; (d) SEQ ID NO:4; (e) SEQ ID NO:5; (f) SEQ ID NO:6, (g) a mixture of SEQ ID NO:6 and SEQ ID NO:7; (h) SEQ ID NO:8; (i) SEQ ID NO:9; (j) SEQ ID NO:10; (k) SEQ ID NO:11; (l) SEQ ID NO:12; (m) SEQ ID NO:13; and (n) SEQ ID NO:14.

In one preferred embodiment of the invention, the VLP is a mosaic VLP comprising or alternatively consisting of more than one amino acid sequence, preferably two amino acid sequences, of coat proteins, mutants or fragments thereof, of a RNA phage.

In one very preferred embodiment, the VLP comprises or alternatively consists of two different coat proteins of a RNA phage, said two coat proteins have an amino acid sequence of SEQ ID NO: 1 and SEQ ID NO:2, or of SEQ ID NO:6 and SEQ ID NO:7.

In preferred embodiments of the present invention, the virus-like particle of the invention comprises, or alternatively consists essentially of, or alternatively consists of recombinant coat proteins, mutants or fragments thereof, of the RNA-bacteriophage Qβ, fr, AP205 or GA. In one preferred embodiment, the VLP is of an RNA-bacteriophage, preferably of an RNA-bacteriophage Qβ, fr, AP205 or GA.

In one preferred embodiment, the VLP of the invention is a VLP of RNA-phage Qβ. The capsid or virus-like particle of Qβ showed an icosahedral phage-like capsid structure with a diameter of 25 nm and T=3 quasi symmetry. The capsid contains 180 copies of the coat protein, which are linked in covalent pentamers and hexamers by disulfide bridges (Golmohammadi, R. et al., Structure 4:543-5554 (1996)), leading to a remarkable stability of the Qβ capsid. Capsids or VLPs made from recombinant Qβ coat protein may contain, however, subunits not linked via disulfide bonds to other subunits within the capsid, or incompletely linked. The capsid or VLP of Qβ shows unusual resistance to organic solvents and denaturing agents. Surprisingly, we have observed that DMSO and acetonitrile concentrations as high as 30%, and guanidinium concentrations as high as 1 M do not affect the stability of the capsid. The high stability of the capsid or VLP of Qβ is an advantageous feature, in particular, for its use in immunization and vaccination of mammals and humans in accordance of the present invention.

Further preferred virus-like particles of RNA-phages, in particular of Qβ and fr in accordance of this invention are disclosed in WO 02/056905, the disclosure of which is herewith incorporated by reference in its entirety. Particular example 18 of WO 02/056905 gave detailed description of preparation of VLP particles from Qβ.

In another preferred embodiment, the VLP of the invention is a VLP of RNA phage AP205. Assembly-competent mutant forms of AP205 VLPs, including AP205 coat protein with the substitution of proline at amino acid 5 to threonine, may also be used in the practice of the invention and leads to other preferred embodiments of the invention. WO 2004/007538 describes, in particular in Example 1 and Example 2, how to obtain VLP comprising AP205 coat proteins, and hereby in particular the expression and the purification thereto. WO 2004/007538 is incorporated herein by way of reference. AP205 VLPs are highly immunogenic, and can be linked with Fel d1 of the invention to typically and preferably generate vaccine constructs displaying the Fel d1 of the invention oriented in a repetitive manner. High antibody titer is elicited against the so displayed Fel d1 of the inventions showing that linked Fel d1 of the inventions are accessible for interacting with antibody molecules and are immunogenic.

In one preferred embodiment, the VLP of the invention comprises or consists of a mutant coat protein of a virus, preferably a RNA phage, wherein the mutant coat protein has been modified by removal of at least one lysine residue by way of substitution and/or by way of deletion. In another preferred embodiment, the VLP of the invention comprises or consists of a mutant coat protein of a virus, preferably a RNA phage, wherein the mutant coat protein has been modified by addition of at least one lysine residue by way of substitution and/or by way of insertion. The deletion, substitution or addition of at least one lysine residue allows varying the degree of coupling, i.e. the amount of Fel d1 of the invention per subunits of the VLP of a virus, preferably of a RNA-phages, in particular, to match and tailor the requirements of the vaccine.

In one preferred embodiment, the compositions and vaccines of the invention have an antigen density being from 0.5 to 4.0. The term “antigen density”, as used herein, refers to the average number of Fel d1 of the invention which is linked per subunit, preferably per coat protein, of the VLP, and hereby preferably of the VLP of a RNA phage. Thus, this value is calculated as an average over all the subunits or monomers of the VLP, preferably of the VLP of the RNA-phage, in the composition or vaccines of the invention.

VLPs or capsids of Qβ coat protein display a defined number of lysine residues on their surface, with a defined topology with three lysine residues pointing towards the interior of the capsid and interacting with the RNA, and four other lysine residues exposed to the exterior of the capsid. Preferably, the at least one first attachment site is a lysine residue, pointing to or being on the exterior of the VLP.

Qβ mutants, of which exposed lysine residues are replaced by arginines can be used for the present invention. Thus, in another preferred embodiment of the present invention, the virus-like particle comprises, consists essentially of or alternatively consists of mutant Qβ coat proteins. Preferably these mutant coat proteins comprise or alternatively consist of an amino acid sequence selected from the group of a) Qβ-240 (SEQ ID NO:15, Lys13-Arg of SEQ ID NO: 1) b) Qβ-243 (SEQ ID NO:16, Asn10-Lys of SEQ ID NO:1); c) Qβ-250 (SEQ ID NO:17, Lys2-Arg of SEQ ID NO:1) d) Qβ-251 (SEQ ID NO:18, Lys16-Arg of SEQ ID NO:1); and e) Qβ-259" (SEQ ID NO:19, Lys2-Arg, Lys16-Arg of SEQ ID NO:1). The construction, expression and purification of the above indicated Qβ mutant coat proteins, mutant Qβ coat protein VLPs and capsids, respectively, are described in WO 02/056905. In particular is hereby referred to Example 18 of above mentioned application.

In another preferred embodiment of the present invention, the virus-like particle comprises, or alternatively consists essentially of, or alternatively consists of mutant coat protein of Qβ, or mutants or fragments thereof, and the corresponding A1 protein. In a further preferred embodiment, the virus-like particle comprises, or alternatively consists essentially of, or alternatively consists of mutant coat protein with amino acid sequence SEQ ID NO:15, 16, 17, 18, or 19 and the corresponding A1 protein.

Further RNA phage coat proteins have also been shown to self-assemble upon expression in a bacterial host (Kastelein, R A. et al., Gene 23:245-254 (1983), Kozlovskaya, T M. et al., Dokl. Akad. Nauk SSSR 287:452-455 (1986), Adhin, M R. et al., Virology 170:238-242 (1989), Priano, C. et al., J. Mol. Biol. 249:283-297 (1995)). In particular the biological and biochemical properties of GA (Ni, C Z., et al., Protein Sci. 5:2485-2493 (1996), Tars, K et al., J. Mol. Biol. 271:759-773 (1997)) and of fr (Pushko P. et al., Prot. Eng. 6:883-891 (1993), Liljas, L et al. J Mol. Biol. 244:279-290, (1994)) have been disclosed. The crystal structure of several RNA bacteriophages has been determined (Golmohammadi, R. et al., Structure 4:543-554 (1996)). Using such information, surface exposed residues can be identified and, thus, RNA-phage coat proteins can be modified such that one or more reactive amino acid residues can be inserted by way of insertion or substitution. Another advantage of the VLPs derived from RNA phages is their high expression yield in bacteria that allows production of large quantities of material at affordable cost.

In one preferred embodiment, the composition of the invention comprises at least one antigen, wherein said at least one antigen is a Fel d1 protein.

In one preferred embodiment, the Fel d1 protein comprising or alternatively consisting of a naturally occurring Fel d1. The primary structure of chain 1 is the sequence of SEQ ID NO 22. Reported variants of chain 1 are Lys29-Arg or Asn, Val33-Ser, Val60-Leu. The primary structure of chain 2 is the sequence of SEQ ID NO 23, 25 or 26. Reported variants of chain 2 are Cys7-Phe, Phe15-Thr, Asn19-Ser, Gly20-Leu, Ile55-Val, Arg57-Lys, Val58-Phe of SEQ ID NO:23, 25 or 26. Further variants of chain 2 are Glu69-Val, Tyr70-Asp, Met72-Thr, Gln-77-Glu and Asn86-Lys of SEQ ID NO:25; Met74-Thr, Gln79-Glu and Asn88-Lys of SEQ ID NO:23. (Griffith I. J. et al, Gene 113:263-268 (1992); Morgenstern J. P. et al, Proc. Natl. Acad. Sci. U.S.A. 88:9690-9694 (1991). Duffort O. A., et al Mol. Immunol. 28:301-309 (1991); Leitermann K., et al, J. Allergy Clin. Immunol. 74:147-153 (1984); Kristensen, A. K, et al. (1997) Biol Chem 378, 899-908). Naturally occurring Fel d1 is obtained by purifying from, for example, cat saliva, cat dander, house dust of a house where a cat lives, etc.

In one preferred embodiment, the Fel d1 of the invention is a recombinant Fel d1 protein or a recombinant Fel d1 fragment. Recombinant Fel d1 protein or recombinant Fel d1 fragment, as used herein, refers to a Fel d1 protein or a Fel d1 fragment that is obtained by a process which comprises at least one step of recombinant DNA technology. The terms "recombinant Fel d1 d1 protein or recombinant Fel d1 fragment" and "Fel d1 d1 protein recombinantly produced or Fel d1 fragment recombinantly produced" are interchangeably used herein and should have the identical meaning. Recombinant Fel d1 d1 protein or fragment can be produced in either prokaryotic expression systems, such as E. coli (WO 2004/094639) or in eukaryotic expression systems, such as baculovirus (WO 00/20032). Seppälä et al disclosed the expression of chain 1 and chain 2 of Fel d1 simultaneously by dicistronic promoter in baculovirus (J. Biol. Chem. November, 2004). Recombinantly produced Fel d1 protein or fragment can be glycosylated or non-glycosylated, depending on the host cell used to produce the recombinant protein.

In one embodiment, the recombinant Fel d1 protein comprises or alternatively consists of chain 1 of Fel d1 and chain 2 of Fel d1, wherein said chain 1 of Fel d1 is associated with chain 2 of Fel d1 exclusively by non-covalent bond, such as hydrophobic interactions.

In one preferred embodiment, the recombinant Fel d1 protein comprises or alternatively consists of chain 1 of Fel d1 and chain 2 of Fel d1, wherein said chain 1 of Fel d1 is associated with chain 2 of Fel d1 by at least one covalent bond. In one preferred embodiment, the at least one covalent bond is a non-peptide bond, wherein said non-peptide is a disulfide bond or wherein preferably said non-peptide is a disulfide bond. For example, Chain 1 of Fel d1 and chain 2 of Fel d1 can be expressed separately and then combined under condition which allows the correct disulfide bond formation, such as reshuffling method. Alternatively chain 1 of Fel d1 and chain 2 of Fel d1 can be expressed simultaneously in one host, for example by cloning the genes encoding chain 1 of Fel d1 and chain 2 of Fel d1, respectively, under two promoters in one plasmid. In eukaryotic expression system, chain 1 of Fel d1 and chain 2 of Fel d1 can be transcribed into one mRNA and translated separately by internal ribosome entry site (IRES).

In one preferred embodiment, the Fel d1 protein comprises or alternatively consists of a fusion protein, wherein said fusion protein comprising chain 1 of Fel d1 and chain 2 of Fel d1. In one preferred embodiment, said chain 1 of Fel d1 and said chain 2 of Fel d1 are fused directly via one peptide bond, which links the N-terminus of one chain with the C-terminus of another chain. In another preferred embodiment, said chain 1 of Fel d1 and said chain 2 of Fel d1 are fused via a spacer, which links the N-terminus of one chain with the C-terminus of another chain. Preferably said spacer has from 1-30, preferably 1-25, preferably 1-20, preferably 1-15, preferably 1-9, preferably 1-5, preferably 1-3 amino acids. Alternatively said spacer has from 10-30, preferably 10-25, more preferably 10-20, more preferably 13-20, more preferably 15-20, more preferably 13-17, more preferably 15-17 amino acids. Preferably said spacer consists of an amino acid sequence having 10, 11, 12, 13, 14, 15, 16, 17, 18, 19, or amino acid residues. In one preferred embodiment, said spacer has 15 amino acids. In one further preferred embodiment, said spacer is (GGGGS)$_3$.

In one preferred embodiment, the fusion protein comprises an amino acid sequence selected from the group consisting of: (a) SEQ ID NO: 24; (b) SEQ ID NO:54; (c) SEQ ID NO:55; (d) SEQ ID NO:56; and (e) SEQ ID NO:57.

In one preferred embodiment, said chain 2 of Fel d1 is fused via its C-terminus to the N-terminus of chain 1 of Fel d1 either directly or via a spacer. In one further preferred embodiment, said Fel d1 protein comprises or alternatively consists of amino acid sequence as of SEQ ID NO:24.

WO 2004/094639 disclosed a recombinant folded Fel d1 with molecular and biological properties similar to the natural counterpart and specifically a synthetic gene coding for a direct fusion of Fel d1 chain 2 N-terminally to chain 1. E. coli expression resulted in a non-covalently associated homodimer with an apparent molecular weight of 30 kDa defined by size exclusion chromatography, each 19177 Da subunit displayed a disulfide pattern identical to that found in the natural Fel d1, and having identical fold of natural and recombinant Fel d1. The recombinant Fel d1 reacted similarly to IgE from sera of cat allergic patients as the natural Fel d1. Thus, this Fel d1 fusion protein mimics the antigenecity of natural Fel d1.

In one preferred embodiment the chain 1 of Fel d1 is fused via its C-terminus to the N-terminus of chain 2 of Fel d1 either directly or via a spacer.

In one preferred embodiment, the chain 1 of Fel d 1 comprises or alternatively consists of sequence of SEQ ID NO: 22 or a homologue sequence thereof, wherein said homologue sequence has an identity to SEQ ID NO: 22 of greater than 80%, preferably greater than 90%, or even more preferably greater than 95%.

In one preferred embodiment, said chain 2 of Fel d 1 comprises or alternatively consists of sequence of SEQ ID NO: 23, SEQ ID NO: 25 or SEQ ID NO: 26, or a homologue sequence thereof, wherein said homologue sequence has an identity to SEQ ID NO: 23, SEQ ID NO: 25 or SEQ ID NO: 26 of greater than 80%, preferably greater than 90%, and even more preferably greater than 95%.

In one preferred embodiment, Fel d1 protein is a recombinant Fel d1 protein, wherein at least one disulfide bond is disrupted, preferably by mutation, more preferably by conservative substitution, such as Cys to Ser. Three inter-chain disulfide bridges linking the two peptides in native Fel d 1 have been identified, i.e. Cys3(1)-Cys73(2), Cys44(1)-48Cys(2) and Cys70(1)-Cys7(2), suggesting an anti-parallel orientation of Fel d 1 peptides. (Kristensen, A. K., et al. (1997) Biol Chem 378, 899-908). In one preferred embodiment, one such disulfide bond of Fel d 1 protein is disrupted. In one further preferred embodiment, two such disulfide bonds of Fel d1 protein are disrupted. In one still further preferred embodiment, all three such disulfide bonds of Fel d1 protein are disrupted. In one preferred embodiment, Cys70 of chain 1 is either deleted or mutated. In another preferred embodiment, Cys 73 of chain is deleted or mutated. In one preferred embodiment, said Fel d1 protein is a fusion protein comprising chain 1 of Fel d1 and chain 2 of Fel d1 fused either directly or via a spacer, wherein all three such disulfide bonds are disrupted. In one further preferred embodiment, said Fel d1 protein comprising or alternatively consisting amino acid sequence as of SEQ ID NO:24, 55 or 57, in which at least one, preferably at least three, even more preferably at least five cysteines are removed by substitution or by deletion.

In one preferred embodiment, the antigen of the invention comprises or alternatively consists of a Fel d1 fragment. It is known that possession of immunogenecity does not usually require the full length of a protein and usually a protein contains more than one antigenic epitope, i.e. antigenic site. A fragment or a short peptide may be sufficient to contain at least one antigenic site that can be bound immunospecifically by an antibody or by a T-cell receptor within the context of an MHC molecule. Antigenic site or sites can be determined by a number of techniques generally known to the skilled person in the art. It can be done by sequence alignment and structure prediction. By way of example, one can predict possible α-helices, turns, inter- and intra-chain disulfide bonds, etc. using a program such as Rasmol. One can further predict sequences that are buried within the molecule or sequences that are exposed on the surface of the molecule. Sequences exposed on the surface of the molecule are more likely to comprise natural antigenic site(s), and thus are useful in inducing therapeutic antibodies. After a surface peptide sequence has been determined, the antigenic site within this sequence can be further defined by, for example, exhaustive mutagenesis method (such as alanine scanning mutagenesis, Cunningham B C, Wells J A. Science 1989 Jun. 2; 244(4908): 1081-5). Briefly amino acids within this sequence are mutated to alanine one by one and the amino acids whose alanine mutations show respectively reduced binding to an antibody (raised against the wild type sequence) or lose totally the binding are likely component of the antigenic site. Another method of determining antigenic site(s) is to generate overlapping peptides that covers the full-length sequence of Fel d1 (Geysen, PNAS Vol 81: 3998-4002, (1984) and Slootstra, J. W. et al., (1996) Mol. Divers. 1, 87-96).

In one preferred embodiment, the antigen of the invention comprises or alternatively consists of at least one, preferably at least two Fel d1 epitopes, further preferably at least one epitope derives from chain 1 of Fel d1 and at least one epitoep derives from chain 2 of Fel d1.

The T-cell reactive epitopes of Fel d1 have been mapped throughout the Fel d1 protein and have been disclosed in prior arts, such as in U.S. Pat. No. 6,120,769, the fourth paragraph of column 14, in column 130 and 131 of U.S. Pat. No. 6,025,162 and these disclosures are incorporated herein by way of reference. In a preferred embodiment, T cell epitope of Fel d1 is selected from a group consisting of: SEQ ID NO: 27-32.

The present invention provides for a method of producing the composition of the invention comprising (a) providing a VLP with at least one first attachment site; (b) providing at least one antigen, wherein said antigen is a Fel d1 protein or a Fel d1 fragment, with at least one second attachment site; and (c) combining said VLP and said at least one antigen to produce said composition, wherein said at least one antigen and said VLP are linked through the first and the second attachment sites. In a preferred embodiment, the provision of the at least one antigen, i.e. a Fel d1 protein or a Fel d1 fragment, with the at least one second attachment site is by way of expression, preferably by way of expression in a bacterial system, preferably in E. coli. Usually tag, such as His tag, Myc tag is added to facilitate the purification process. In another approach particularly the Fel d1 fragments with no longer than 50 amino acids can be chemically synthesized.

In one preferred embodiment of the invention, the VLP with at least one first attachment site is linked to the Fel d1 of the invention with at least one second attachment site via at least one peptide bond. Gene encoding Fel d1 of the invention, preferably Fel d1 fragment, more preferably a fragment not longer than 50 amino acids, even more preferably less than 30 amino acids, is in-frame ligated, either internally or preferably to the N- or the C-terminus to the gene encoding the coat protein of the VLP. Embodiments of using antigen of the invention to coat protein, mutants or fragments thereof, to a coat protein of a virus have been disclosed in WO 2004/

009124 page 62 line 20 to page 68 line 17 and herein are incorporated by way of reference.

In one preferred embodiment, a Fel d1 fragment is fused to either the N- or the C-terminus of a coat protein, mutants or fragments thereof, of RNA phage AP205. In one further preferred embodiment, the fusion protein further comprises a spacer, wherein said spacer is fused to the coat protein, fragments or mutants thereof, of AP205 and a Fel d1 fragment.

In one preferred embodiment of the present invention, the composition comprises or alternatively consists essentially of a virus-like particle with at least one first attachment site linked to at least one Fel d1 of the invention with at least one second attachment site via at least one covalent bond, preferably the covalent bond is a non-peptide bond. In a preferred embodiment of the present invention, the first attachment site comprises, or preferably is, an amino group, preferably the amino group of a lysine residue. In another preferred embodiment of the present invention, the second attachment site comprises, or preferably is, a sulfhydryl group, preferably a sulfhydryl group of a cysteine.

In a very preferred embodiment of the invention, the at least one first attachment site is an amino group, preferably an amino group of a lysine residue and the at least one second attachment site is a sulfhydryl group, preferably a sulfhydryl group of a cysteine.

In one preferred embodiment of the invention, the Fel d1 of the invention is linked to the VLP by way of chemical cross-linking, typically and preferably by using a heterobifunctional cross-linker. In preferred embodiments, the heterobifunctional cross-linker contains a functional group which can react with the preferred first attachment sites, preferably with the amino group, more preferably with the amino groups of lysine residue(s) of the VLP, and a further functional group which can react with the preferred second attachment site, i.e. a sulfhydryl group, preferably of cysteine(s) residue inherent of, or artificially added to the Fel d1 of the invention, and optionally also made available for reaction by reduction. Several hetero-bifunctional cross-linkers are known to the art. These include the preferred cross-linkers SMPH (Pierce), Sulfo-MBS, Sulfo-EMCS, Sulfo-GMBS, Sulfo-SIAB, Sulfo-SMPB, Sulfo-SMCC, SVSB, SIA and other cross-linkers available for example from the Pierce Chemical Company, and having one functional group reactive towards amino groups and one functional group reactive towards sulfhydryl groups. The above mentioned cross-linkers all lead to formation of an amide bond after reaction with the amino group and a thioether linkage with the sulfhydryl groups. Another class of cross-linkers suitable in the practice of the invention is characterized by the introduction of a disulfide linkage between the Fel d1 of the invention and the VLP upon coupling. Preferred cross-linkers belonging to this class include, for example, SPDP and Sulfo-LC-SPDP (Pierce).

In a preferred embodiment, the composition of the invention further comprises a linker. Engineering of a second attachment site onto the Fel d1 of the invention is achieved by the association of a linker, preferably containing at least one amino acid suitable as second attachment site according to the disclosures of this invention. Therefore, in a preferred embodiment of the present invention, a linker is associated to the Fel d1 of the invention by way of at least one covalent bond, preferably, by at least one, typically one peptide bond. Preferably, the linker comprises, or alternatively consists of, the second attachment site. In a further preferred embodiment, the linker comprises a sulfhydryl group, preferably of a cysteine residue. In another preferred embodiment, the amino acid linker is a cysteine residue.

The selection of a linker will be dependent on the nature of the Fel d1 of the invention, on its biochemical properties, such as pI, charge distribution and glycosylation. In general, flexible amino acid linkers are favored. In a further preferred embodiment of the present invention, the linker consists of amino acids, wherein further preferably the linker consists of at most 25, preferably at most 20, more preferably at most 15 amino acids. In an again preferred embodiment of the invention, the amino acid linker contains no more than 10 amino acids. Preferred embodiments of the linker are selected from the group consisting of: (a) CGG; (b) N-terminal gamma 1-linker (e.g. CGDKTHTSPP, SEQ ID NO:58); (c) N-terminal gamma 3-linker (e.g. CGGPKPSTPPGSSGGAP, SEQ ID NO:69); (d) Ig hinge regions; (e) N-terminal glycine linkers (e.g. GCGGGG, SEQ ID NO:59); (f) (G)kC(G)n with n=0-12 and k=0-5; (g) N-terminal glycine-serine linkers ((GGGGS) n, n=1-3 with one further cysteine, (for example SEQ ID NO:60, which corresponds to an embodiment wherein n=1); (h) (G)kC(G)m(S)l(GGGGS)n with n=0-3, k=0-5, m=0-10, l=0-2 (for example SEQ ID NO:61, which corresponds to an embodiment wherein n=1, k=1, l=1 and m=1); (i) GGC; (k) GGC-NH2; (l) C-terminal gamma 1-linker (e.g. DKTHTSPPCG, SEQ ID NO:62); (m) C-terminal gamma 3-linker (e.g. PKPSTPPGSSGGAPGGCG, SEQ ID NO:63); (n) C-terminal glycine linkers (GGGGCG, SEQ ID NO:64); (o) (G)nC (G)k with n=0-12 and k=0-5; (p) C-terminal glycine-serine linkers ((SGGGG)n n=1-3 with one further cysteine, (for example SEQ ID NO:65, which corresponds to an embodiment wherein n=1)); (q) (G)m(S)l(GGGGS)n(G)oC(G)k with n=0-3, k=0-5, m=0-10, l=0-2, and o=0-8 (for example SEQ ID NO:66, which corresponds to an embodiment wherein n=1, k=1, l=1, o=1 and m=1). In a further preferred embodiment the linker is added to the N-terminus of Fel d1 of the invention. In another preferred embodiment of the invention, the linker is added to the C-terminus of Fel d1 of the invention.

Preferred linkers according to this invention are glycine linkers (G)n further containing a cysteine residue as second attachment site, such as N-terminal glycine linker (GCGGGG) and C-terminal glycine linker (GGGGCG). Further preferred embodiments are C-terminal glycine-lysine linker (GGKKGC, SEQ ID NO:67) and N-terminal glycine-lysine linker (CGKKGG, SEQ ID NO:68), GGCG a GGC or GGC-NH2 ("NH2" stands for amidation) linkers at the C-terminus of the peptide or CGG at its N-terminus. In general, glycine residues will be inserted between bulky amino acids and the cysteine to be used as second attachment site, to avoid potential steric hindrance of the bulkier amino acid in the coupling reaction.

In one preferred embodiment, the linker is fused to the N-terminus of Fel d1 protein or Fel d1 fragment. In one further preferred embodiment, the linker is GCGG. In another preferred embodiment, the linker is fused to the C-terminus of Fel d1 protein or Fel d1 fragment. In one further preferred embodiment, the linker is GGC. In the case of Fel d1 protein or Fel d1 fragment consisting of two polypeptide chains, such Fel d1 protein or Fel d1 fragment has two N-terminus and two C-terminus. The linker may be fused to both of the two N-terminus or to both of the C-terminus. Preferably the linker is fused to only one of the two N-terminus or only one of the two C-terminus.

Linking of the Fel d1 of the invention to the VLP by using a hetero-bifunctional cross-linker according to the preferred methods described above, allows coupling of the Fel d1 of the invention to the VLP in an oriented fashion. Other methods of linking the Fel d1 of the invention to the VLP include methods wherein the Fel d1 of the invention is cross-linked to the VLP, using the carbodiimide EDC, and NHS. The Fel d1 of the invention may also be first thiolated through reaction, for example with SATA, SATP or iminothiolane. The Fel d1 of the invention, after deprotection if required, may then be coupled to the VLP as follows. After separation of the excess thiolation reagent, the Fel d1 of the invention is reacted with the VLP, previously activated with a hetero-bifunctional cross-linker comprising a cysteine reactive moiety, and therefore displaying at least one or several functional groups reactive towards cysteine residues, to which the thiolated Fel d1 of the invention can react, such as described above. Optionally, low amounts of a reducing agent are included in the reaction mixture. In further methods, the Fel d1 of the invention is attached to the VLP, using a homo-bifunctional cross-linker such as glutaraldehyde, DSG, BM[PEO]4, BS3, (Pierce) or other known homo-bifunctional cross-linkers with functional groups reactive towards amine groups or carboxyl groups of the VLP.

In other embodiments of the present invention, the composition comprises or alternatively consists essentially of a virus-like particle linked to Fel d1 of the invention via chemical interactions, wherein at least one of these interactions is not a covalent bond. For example, linking of the VLP to the Fel d1 of the invention can be effected by biotinylating the VLP and expressing the Fel d1 of the invention as a streptavidin-fusion protein.

One or several antigen molecules, i.e. Fel d1 of the invention, can be attached to one subunit of the VLP, preferably of RNA phage coat proteins, preferably through the exposed lysine residues of the coat proteins of RNA phage VLP, if sterically allowable. A specific feature of the VLPs of RNA phage and in particular of the Qβ coat protein VLP is thus the possibility to couple several antigens per subunit. This allows for the generation of a dense antigen array.

In very preferred embodiments of the invention, the Fel d1 of the invention is linked via a cysteine residue, having been added to either the N-terminus or the C-terminus of the Fel d1 of the invention, or a natural cysteine residue within the Fel d1 of the invention, to lysine residues of coat proteins of the VLPs of RNA phage, and in particular to the coat protein of Qβ.

As described above, four lysine residues are exposed on the surface of the VLP of Qβ coat protein. Typically and preferably these residues are derivatized upon reaction with a cross-linker molecule. In the instance where not all of the exposed lysine residues can be coupled to an antigen, the lysine residues which have reacted with the cross-linker are left with a cross-linker molecule attached to the ε-amino group after the derivatization step. This leads to disappearance of one or several positive charges, which may be detrimental to the solubility and stability of the VLP. By replacing some of the lysine residues with arginines, as in the disclosed Qβ coat protein mutants, we prevent the excessive disappearance of positive charges since the arginine residues do not react with the preferred cross-linkers. Moreover, replacement of lysine residues by arginine residues may lead to more defined antigen arrays, as fewer sites are available for reaction to the antigen.

Accordingly, exposed lysine residues were replaced by arginines in the following Qβcoat protein mutants: Qβ240 (Lys13-Arg; SEQ ID NO:15), Qβ-250 (Lys 2-Arg, Lys13-Arg; SEQ ID NO:17), Qβ-259 (Lys 2-Arg, Lys16-Arg; SEQ ID NO:19) and Qβ-251; (Lys16-Arg, SEQ ID NO:18). In a further embodiment, we disclose a Qβ mutant coat protein with one additional lysine residue Qβ-243 (Asn 10-Lys; SEQ ID NO:16), suitable for obtaining even higher density arrays of antigens.

In one preferred embodiment of the invention, the VLP of the invention is recombinantly produced by a host and wherein said VLP is essentially free of host RNA, preferably host nucleic acids. In one further preferred embodiment, the composition further comprises at least one polyanionic macromolecule bound to, preferably packaged inside or enclosed in, the VLP. In a still further preferred embodiment, the polyanionic macromolecule is polyglutamic acid and/or polyaspartic acid.

Essentially free of host RNA, preferably host nucleic acids: The term "essentially free of host RNA, preferably host nucleic acids" as used herein, refers to the amount of host RNA, preferably host nucleic acids, comprised by the VLP, which amount typically and preferably is less than 30 μg, preferably less than 20 μg, more preferably less than 10 μg, even more preferably less than 8 μg, even more preferably less than 6 μg, even more preferably less than 4 μg, most preferably less than 2 μg, per mg of the VLP. Host, as used within the afore-mentioned context, refers to the host in which the VLP is recombinantly produced. Conventional methods of determining the amount of RNA, preferably nucleic acids, are known to the skilled person in the art. The typical and preferred method to determine the amount of RNA, preferably nucleic acids, in accordance with the present invention is described in Example 17 of the PCT/EP2005/055009 filed on Oct. 5, 2005 by the same assignee. Identical, similar or analogous conditions are, typically and preferably, used for the determination of the amount of RNA, preferably nucleic acids, for inventive compositions comprising VLPs other than Qβ. The modifications of the conditions eventually needed are within the knowledge of the skilled person in the art. The numeric value of the amounts determined should typically and preferably be understood as comprising values having a deviation of ±10%, preferably having a deviation of ±5%, of the indicated numeric value.

Polyanionic macromolecule: The term "polyanionic macromolecule", as used herein, refers to a molecule of high relative molecular mass which comprises repetitive groups of negative charge, the structure of which essentially comprises the multiple repetition of units derived, actually or conceptually, from molecules of low relative molecular mass. A polyanionic macromolecule should have a molecular weight of at least 2000 Dalton, more preferably of at least 3000 Dalton and even more preferably of at least 5000 Dalton. The term "polyanionic macromolecule" as used herein, typically and preferably refers to a molecule that is not capable of activating toll-like receptors. Thus, the term "polyanionic macromolecule" typically and preferably excludes Toll-like receptors ligands, and even more preferably furthermore excludes immunostimulatory substances such as Toll-like receptors ligands, immunostimulatory nucleic acids, and lipopolysaccharides (LPS). More preferably the term "polyanionic macromolecule" as used herein, refers to a molecule that is not capable of inducing cytokine production. Even more preferably the term "polyanionic macromolecule" excludes immunostimulatory substances. The term "immunostimulatory substance", as used herein, refers to a molecule that is capable of inducing and/or enhancing immune response specifically against the antigen comprised in the present invention.

Host RNA, preferably host nucleic acids: The term "host RNA, preferably host nucleic acids" or the term "host RNA, preferably host nucleic acids, with secondary structure", as used herein, refers to the RNA, or preferably nucleic acids, that are originally synthesized by the host. The RNA, preferably nucleic acids, may, however, undergo chemical and/or physical changes during the procedure of reducing or eliminating the amount of RNA, preferably nucleic acids, typically and preferably by way of the inventive methods, for example, the size of the RNA, preferably nucleic acids, may be shortened or the secondary structure thereof may be altered. However, even such resulting RNA or nucleic acids is still considered as host RNA, or host nucleic acids.

Methods to determine the amount of RNA and to reduce the amount of RNA comprised by the VLP have disclosed in PCT/EP2005/055009 filed by the same assignee on Oct. 5, 2005 and thus the entire application is incorporated herein by way of reference. Reducing or eliminating the amount of host RNA, preferably host nucleic, minimizes or reduces unwanted T cell responses, such as inflammatory T cell response and cytotoxic T cell response, and other unwanted side effects, such as fever, while maintaining strong antibody response specifically against Fel d1.

In one preferred embodiment, this invention provides a method of preparing the inventive compositions and VLP of an RNA-bacteriophage—Fel d1 of the invention, wherein said VLP is recombinantly produced by a host and wherein said VLP is essentially free of host RNA, preferably host nucleic acids, comprising the steps of: a) recombinantly producing a virus-like particle (VLP) with at least one first attachment site by a host, wherein said VLP comprises coat proteins, variants or fragments thereof, of a RNA-bacteriophage; b) disassembling said virus-like particle to said coat proteins, variants or fragments thereof, of said RNA-bacteriophage; c) purifying said coat proteins, variants or fragments thereof; d) reassembling said purified coat proteins, variants or fragments thereof, of said RNA-bacteriophage to a virus-like particle, wherein said virus-like particle is essentially free of host RNA, preferably host nucleic acids; and e) linking at least one antigen of the invention with at least one second attachment site to said VLP obtained from step (d). In a further preferred embodiment, the reassembling of said purified coat proteins, variants or fragments thereof, is effected in the presence of at least one polyanionic macromolecule.

In one preferred embodiment, the composition of the invention further comprises at least one immunostimulatory substance capable of inducing and/or enhancing an immune response. Preferably the immunostimulatory substance is a Toll-like receptor ligand, preferably selected from the group consisting of: (a) immunostimulatory nucleic acids; (b) peptidoglycans; (c) lipopolysaccharides; (d) lipoteichonic acids; (e) imidazoquinoline compounds; (f) flagellines; (g) lipoproteins; (h) immunostimulatory organic molecules; (i) unmethylated CpG-containing oligonucleotides; and (j) any mixtures of substance of (a), (b), (c), (d), (e), (f), (g), (h) and (i).

In a further preferred embodiment, the immunostimulatory nucleic acid is preferably selected from the group consisting of: (a) a nucleic acid of bacterial origin; (b) a nucleic acid of viral origin; (c) a nucleic acid comprising unmethylated CpG motif, (d) a double-stranded RNA; (e) a single stranded RNA; and (g) a nucleic acid free of unmethylated CpG motif. Immunostimulatory nucleic acids that do not contain unmethylated CpG motif have been disclosed in the prior art, for example in WO01/22972. The term “nucleic acid”, as used herein, refers to a molecule composed of linearly covalently linked monomers (nucleotides). It indicates a molecular chain of nucleotides and does not refer to a specific length of the product. Thus, oligonucleotides are included within the definition of nucleic acid. The bond between the nucleotides is typically and preferably phosphodiester bond. Nucleic acids comprising modifications of bonds, for example, phosphorothioate bond, are also encompassed by the present invention.

In one preferred embodiment, the immunostimulatory substance is mixed with the recombinant VLP. In another further preferred embodiment, the immunostimulatory substance is bound to, preferably packaged inside, the VLP of the invention.

Detailed descriptions of immunostimulatory substance, particularly immunostimulatory nucleic acid, more particularly oligonucleotides comprising unmethylated CpG have been disclosed in WO 03/024480, 03/024481 and PCT/EP/04/003165. Methods of mixing the immunostimulatory substances with the VLP-antigen have disclosed in WO 03/024480. Methods of packaging the immunostimulatory substances inside the VLP have been disclosed in WO 03/024481. The entire applications of WO 03/024480, 03/024481 and PCT/EP/04/003165 are therefore incorporated herein by way of reference. VLP can generally induce and/or enhance the immune system. However, the term “immunostimulatory substance”, as used within the context of this application, refers to an immunostimulatory substance not being the VLP used for the inventive compositions, rather in addition to said VLP.

The inclusion of immunostimulatory substances, preferably immunostimulatory nucleic acids into the composition of the invention may drives the immune responses towards Th1 responses and thereby suppressing the Th2 responses.

In one aspect, the invention provides a vaccine comprising the composition of the invention. In one aspect, the invention provides a vaccine comprising the composition of the invention and a suitable buffer. In one preferred embodiment, the vaccine composition further comprises at least one adjuvant. The administration of the at least one adjuvant may hereby occur prior to, contemporaneously or after the administration of the inventive composition. The term “adjuvant” as used herein refers to non-specific stimulators of the immune response or substances that allow generation of a depot in the host which when combined with the vaccine and pharmaceutical composition, respectively, of the present invention may provide for an even more enhanced immune response.

In another preferred embodiment, the vaccine composition is devoid of adjuvant. An advantageous feature of the present invention is the high immunogenicity of the composition, even in the absence of adjuvants. The avoidance of using adjuvant may reduce a possible occurrence of side effects relating to the using of adjuvants. Thus, the administration of the vaccine of the invention to a patient will preferably occur without administering at least one adjuvant to the same patient prior to, contemporaneously or after the administration of the vaccine.

The invention further discloses a method of immunization comprising administering the vaccine of the present invention to a human and to non-human mammal, such as dog or cat. Without the intention to limit the present invention by the theory, injection of the vaccine composition of the invention to a cat may neutrolizing Fel d1 and therefore reducing the amount of Fel d1 in cat saliva.

The vaccine may be administered by various methods known in the art, but will normally be administered by injection, infusion, inhalation, oral administration, or other suitable physical methods. The conjugates may alternatively be administered intramuscularly, intravenously, transmucosally, transdermally, intranasally, intraperitoneally or subcutaneously. Components of conjugates for administration include sterile aqueous (e.g., physiological saline) or non-aqueous solutions and suspensions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption.

Vaccines of the invention are said to be "pharmacologically acceptable" if their administration can be tolerated by a recipient individual. Further, the vaccines of the invention will be administered in a "therapeutically effective amount" (i.e., an amount that produces a desired physiological effect). The nature or type of immune response is not a limiting factor of this disclosure. Without the intention to limit the present invention by the following mechanistic explanation, the inventive vaccine might induce antibodies, presumably IgG subtypes, which bind to Fel d1 and thus preventing Fel d1 to be seen by IgE bound to mast cells and basophils. Alternatively or simultaneously, the composition of the present invention drives the immune responses towards Th1 responses, suppressing the development of Th2 responses and hence the production of IgE antibodies, a major component in allergic reactions.

In one aspect, the invention provides a pharmaceutical composition comprising the composition as taught in the present invention and an acceptable pharmaceutical carrier. When vaccine of the invention is administered to an individual, it may be in a form which contains salts, buffers, adjuvants, or other substances which are desirable for improving the efficacy of the conjugate. Examples of materials suitable for use in preparation of pharmaceutical compositions are provided in numerous sources including REMINGTON'S PHARMACEUTICAL SCIENCES (Osol, A, ed., Mack Publishing Co., (1990)).

The invention teaches a process for producing the composition of the invention comprising the steps of: (a) providing a core particle with at least one first attachment site, wherein said core particle is a virus-like particle or a virus particle; (b) providing at least one antigen with at least one second attachment site, wherein said at least antigen is a Fel d1 protein or a Fel d1 fragment, and (c) combining said core particle and said at least one antigen to produce a composition, wherein said at least one antigen and said core particle are linked through the first and the second attachment sites.

In a further preferred embodiment, the step of providing core particle with at least one first attachment site comprises further steps: (a) disassembling said core particle to coat proteins, mutants or fragments thereof, of said core particle; (b) purifying said coat proteins, mutants or fragments thereof; (c) reassembling said purified coat proteins, mutants or fragments thereof, of said core particle, wherein said core particle is essentially free of host RNA, preferably host nucleic acids. In a still further preferred embodiment, the reassembling of said purified coat proteins is effected in the presence of at least one polyanionic macromolecule or at least one immunostimuolatory nucleic acids.

In one aspect, the invention provides a method of using the compositions of the invention for preventing and/or treating cat allergy in a mammal, wherein preferably said mammal is a human or a dog.

In one aspect, the invention teaches the use of the inventive composition as a medicament. In another aspect, the invention provides for the use of the composition of the invention for the manufacture of a medicament for treatment of cat allergy in a mammal, wherein preferably said mammal is a human or a dog.

In one aspect, this invention provides a Fel d1 fusion protein comprising chain 1 of Fel d1 and chain 2 of Fel d1 fused via an amino acid spacer, which links the N-terminus of one chain with the C-terminus of another chain, wherein said amino acid spacer consists of an amino acid sequence having 10-30, preferably 10-25, preferably 10-20, preferably 13-20, preferably 15-20, preferably 13-17, preferably 15-17 amino acid residues, and wherein said fusion protein is not a fusion protein comprising chain 1 of SEQ ID NO:22 fused through (GGGGS)$_3$ to the N-terminus of chain 2 of SEQ ID NO:23, 25 or 26 and wherein said disclaimed fusion protein is expressed in baculovirus expression system.

WO2004094639 discloses Fel d1 fusion protein by linking chain 1 and chain 2 with a linker selected from a carbon-nitrogen bond and a short peptide, i.e. having from 1 to 9, preferably 1 to 5, particular preferably 1 to 3 amino acids. It further states that surprisingly a bond or a short peptide does not induce significant constrains or unfolding. However WO2004094639 faisl to disclose linker longer than 9 amino acids.

WO 00/20032 discloses the baculovirus expressed recombinant Fel d1 comprising chain 1 and chain 2 expressed in series and linked together by a glycine/serine linker (GGGGS)$_3$. WO 00/20032 also reported that the immunoreactivity of rFel d1 for IgG and IgE antibody is improved dramatically by expressing the allergen in baculovirus, compared with the allergen expressed in E. coli.

The Fel d1 fusion protein of the invention can be produced either in a prokaryotic expression system or in an eukaryotic expression system, such as a baculovirus system. In one preferred embodiment, said Fel d1 fusion protein of the invention is produced from E. coli.

In one preferred embodiment, the spacer comprised by the Fel d1 fusion protein of the invention consists of an amino acid sequence having 10, 11, 12, 13, 14, 15, 16, 17, 18, 19, or 20 amino acid residues.

In one preferred embodiment, the spacer comprised by the Fel d1 fusion protein consisting of an amino acid sequence having 2, 3 or 4 times of GGGGS repeat.

In one preferred embodiment, the chain 2 of Fel d1 is at the N-terminus of the fusion protein of the invention.

In another preferred embodiment, the chain 1 of Fel d1 is at the N-terminus of the fusion protein of the invention. In one further preferred embodiment, the fusion protein is produced from E. coli.

In one very preferred embodiment, the Fel d1 fusion protein of the invention comprises an amino acid sequence selected from the group consisting of: (a) SEQ ID NO:54; (b) SEQ ID NO:55; and (c) SEQ ID NO:57. The invention further provides nucleotide sequence encoding the Fel d1 fusion protein of the invention. In one preferred embodiment, the invention provides nucleotide sequence encoding a fusion protein of the invention selected from the group consisting of: (a) SEQ ID NO:54; (b) SEQ ID NO:55; and (c) SEQ ID NO:57. In one further preferred embodiment, the Fel d1 fusion protein of the invention is produced in E. coli. In one further preferred embodiment, the Fel d1 fusion protein of the invention comprises or alternatively consists of an amino acid sequence of SEQ ID NO:57, wherein said fusion protein of the invention is produced in E. coli.

In one aspect, the invention provides for a use of the Fel d1 fusion protein of the invention for diagnosis and treatment of cat allergy.

EXAMPLES

Example 1

Preparation of Qβ VLPs of the Invention by Disassembly/Reassembly in the Presence of Different Polyanionic Macromolecules Resulting in Reassembled Qβ VLPs (A) Disassembly of Prior Art Qβ VLP 45 mg prior art Qβ VLP (2.5 mg/ml, as determined by Bradford analysis) in PBS (20 mM Phosphate, 150 mM NaCl, pH 7.5) purified from *E. coli* lysate was reduced with 10 mM DTT for 15 min at room temperature under stirring conditions. Magnesium chloride was then added to 0.7 M final concentration and the incubation was continued for 15 min at room temperature under stirring conditions, which led to the precipitation of the encapsulated host cell RNA. The solution was centrifuged for 10 min at 4000 rpm at 4° C. (Eppendorf 5810 R, in fixed angle rotor A-4-62 used in all following steps) in order to remove the precipitated RNA from the solution. The supernatant, containing the released, dimeric Qβ coat protein, was used for the chromatographic purification steps.

(B) Purification of the Qβ Coat Protein by Cation Exchange Chromatography and by Size Exclusion Chromatography The supernatant of the disassembly reaction, containing the dimeric coat protein, host cell proteins and residual host cell RNA, was diluted 1:15 in water to adjust conductivity below 10 mS/cm and was loaded onto a SP-Sepharose FF column (xk16/20, 6 ml, Amersham Bioscience). The column was equilibrated beforehand with 20 mM sodium phosphate buffer pH 7. The elution of the bound coat protein was accomplished by a step gradient to 20 mM sodium phosphate/500 mM sodium chloride and the protein was collected in a fraction volume of approx. 25 ml. The chromatography was carried out at room temperature with a flow rate of 5 ml/min and the absorbance was monitored at 260 nm and 280° nm.

In the second step, the isolated Qβ coat protein (the eluted fraction from the cation exchange column) was loaded (in two runs) onto a Sephacryl S-100 HR column (xk26/60, 320 ml, Amersham Bioscience), equilibrated with 20 mM sodium phosphate/250 mM sodium chloride; pH 6.5. The chromatography was carried out at room temperature with a flow rate of 2.5 ml/min and the absorbance was monitored at 260 nm and 280 nm. Fractions of 5 ml were collected.

(C1) Reassembly of the Qβ VLP by Dialysis

Purified Qβ coat protein (2.2 mg/ml in 20 mM sodium phosphate pH 6.5), one polyanionic macromolecule (2 mg/ml in water), urea (7.2 M in water) and DTT (0.5 M in water) were mixed to the final concentrations of 1.4 mg/ml coat protein, 0.14 mg/ml of the respective polyanionic macromolecule, 1 M urea and 2.5 mM DTT. The mixtures (1 ml each) were dialyzed for 2 days at 5° C. in 20 mM TrisHCl, 150 mM NaCl pH 8, using membranes with 3.5 kDa cut off. The polyanionic macromolecules were: polygalacturonic acid (25000-50000, Fluka), dextran sulfate (MW 5000 and 10000, Sigma), poly-L-aspartic acid (MW 11000 and 33400, Sigma), poly-L-glutamic acid (MW 3000, 13600 and 84600, Sigma) and tRNAs from bakers yeast and wheat germ.

(C2) Reassembly of the Qβ VLP by Diafiltration 33 ml purified Qβ coat protein (1.5 mg/ml in 20 mM sodium phosphate pH 6.5, 250 mM NaCl) was mixed with water and urea (7.2 M in water), NaCl (5 M in water) and poly-L-glutamic acid (2 mg/ml in water, MW: 84600). The volume of the mixture was 50 ml and the final concentrations of the components were 1 mg/ml coat protein, 300 mM NaCl, 1.0 M urea and 0.2 mg/ml poly-L-glutamic acid. The mixture was then diafiltrated at room temperature, against 500 ml of 20 mM TrisHCl pH 8, 50 mM NaCl, applying a cross flow rate of 10 ml/min and a permeate flow rate of 2.5 ml/min, in a tangential flow filtration apparatus using a Pellicon XL membrane cartridge (Biomax 5K, Millipore).

Example 2

In Vitro Assembly of AP205 VLPs (A) Purification of AP205 Coat Protein

Disassembly: 20 ml of AP205 VLP solution (1.6 mg/ml in PBS, purified from *E. coli* extract) was mixed with 0.2 ml of 0.5 M DTT and incubated for 30 min at room temperature. 5 ml of 5 M NaCl was added and the mixture was then incubated for 15 min at 60° C., causing precipitation of the DTT-reduced coat proteins. The turbid mixture was centrifuged (rotor Sorvall SS34, 10000 g, 10 min, 20° C.) and the supernatant was discarded and the pellet was dispersed in 20 ml of 1 M Urea/20 mM Na Citrate pH 3.2. After stirring for 30 min at room temperature, the dispersion was adjusted to pH 6.5 by addition of 1.5 M $Na_2HPO_4$ and then centrifuged (rotor Sorvall SS34, 10000 g, 10 min, 20° C.) to obtain supernatant containing dimeric coat protein.

Cation exchange chromatography: The supernatant (see above) was diluted with 20 ml water to adjust a conductivity of approx. 5 mS/cm. The resulting solution was loaded on a column of 6 ml SP Sepharose FF (Amersham Bioscience) which was previously equilibrated with 20 mM sodium phosphate pH 6.5 buffer. After loading, the column was washed with 48 ml of 20 mM sodium phosphate pH 6.5 buffer followed by elution of the bound coat protein by a linear gradient to 1 M NaCl over 20 column volumes. The fractions of the main peak were pooled and analyzed by SDS-PAGE and UV spectroscopy. According to SDS-PAGE, the isolated coat protein was essentially pure from other protein contaminations. According to the UV spectroscopy, the protein concentration was 0.6 mg/ml (total amount 12 mg), taking that 1 A280 unit reflects 1.01 mg/ml of AP205 coat protein. Furthermore, the value of A280 (0.5999) over the value of A260 (0.291) is 2, indicating that the preparation is essentially free of nucleic acids.

(B) Assembly of AP205 VLPs

Assembly in the absence of any polyanionic macromolecule: The eluted protein fraction from above was diafiltrated and concentrated by TFF to a protein concentration of 1 mg/ml in 20 mM sodium phosphate pH 6.5. 500 µl of that solution was mixed with 50 µl of 5 M NaCl solution and incubated for 48 h at room temperature. The formation of reassembled VLPs in the mixture was shown by non-reducing SDS-PAGE and by size exclusion HPLC. A TSKgel G5000 PWXL column (Tosoh Bioscience), equilibrated with 20 mM sodium phosphate, 150 mM NaCl pH 7.2, was used for the HPLC analysis.

Assembly in the presence of polyglutamic acid: 375 µl of purified AP205 coat protein (1 mg/ml in 20 mM sodium phosphate pH 6.5) was mixed with 50 µl of NaCl stock solution (5 M in water) solution, 50 µl of polyglutamic acid stock solution (2 mg/ml in water, MW: 86400, Sigma) and 25 µl of water. The mixture was incubated for 48 h at room temperature. The formation of reassembled VLP in the mixture was shown by non-reducing SDS-PAGE and by size exclusion HPLC. The coat protein in the mixture was almost completely incorporated into the VLPs, showing a higher assembly efficiency than the AP205 coat protein assembled in the absence of any polyanionic macromolecule.

Example 3

Cloning of Fel d1 Fusion Proteins

Genes encoding Fel d1 chain 1 and chain 2, respectively, were made by PCR-amplification using overlapping DNA-primers as shown below. Forward (F) and reverse (R) primers are indicated. Fragments were ligated into pCRII-TOPO vector (Invitrogen) and transformed into XL1-Blue. Inserts of Fel d1 chain 1 and chain 2 were sequence verified.

Primer Sequence 1F: SEQ ID NO:34;

Primer Sequence 2R: SEQ ID NO:35

Primer Sequence 3F: SEQ ID NO:36

Primer Sequence 4R: SEQ ID NO:37

Primer Sequence SF: SEQ ID NO:38

Primer Sequence 6R: SEQ ID NO:39

Primer Sequence 7F: SEQ ID NO:40

Primer Sequence 8R: SEQ ID NO:41

Primer Sequence 9F: SEQ ID NO:42

Primer Sequence 10R: SEQ ID NO:43

Fel d1 Fusion Constructs:

FELD1 refers to the protein with chain 2 at the N-terminus fused directly with chain 1. Nucleotide sequences encoding FELD 1 was created by splicing overlap extension (SOE) PCR using primer 11 linker (SEQ ID NO:44).

FD12 refers to the protein with chain 1 at the N-terminus fused directly with chain 2. Nucleotide sequence encoding FD12 was created by splicing overlap extension (SOE) PCR using primers 12-1 (SEQ ID NO:45), 12-3 (SEQ ID NO:46) and 12-2-1 (SEQ ID NO:47).

FELD1-10aa and FELD1-15aa refer to proteins with chain 2 at the N-terminus fused via a 10 $(GGGGS)_2$ or 15 $(GGGGS)_3$ amino acid spacer, respectively, with the chain 1 at the C-terminus. Plasmid containing nucleotide sequence encoding FELD1 was used as template to create the 10 amino acids or the 15 amino acids spacer by inverse PCR mutagenesis (IPCRM). For the 1-15 spacer two primers (primer 1-10aa, SEQ ID NO:48 and primer 2-5aa, SEQ ID NO:49) were used. For the 1-10 spacer two primers (primer 1-5aa, SEQ ID NO:50 and primer 2-5aa). The resulting PCR fragment was circularized by ligation. It is resistant to Dpn I digestion, which only recognizes sequence containing methylated adenine, while the plasmid template was digested by Dpn I.

FD12-10aa and FD12-15aa refer to proteins with chain 1 at the N-terminus fused via a 10 $(GGGGS)_2$ or 15 $(GGGGS)_3$ amino acid spacer, respectively, with the chain 2 at the C-terminus. Fusion FD12-10aa and FD12-15aa were similarly produced as described above. For the 15 amino acid spacer primer FD2-10aa (SEQ ID NO:51) and primer FD1-5 aa (SEQ ID NO:52) were used. For 10 amino acid spacer primer FD1-5aa and FD2-5 aa (SEQ ID NO:53) were used.

Example 4

Bacterial Expression and Purification of his-Tagged Fel D1 Fusion Proteins

The nucleotide sequences encoding various Fel d1 fusion constructs as described in EXAMPLE 3 were subcloned into a T7 based expression system pET-42T(+), modified from plasmid pET-42a(+) (Novagen). The C-terminus of the fusion constructs were fused to a His-tag sequence followed by GGC, an amino acid linker containing cysteine as the second attachment site. The resulting constructs are named accordingly by adding "-HC" at the end.

FELD1-HC, FELD1-10aa-HC and FELD1-15aa-HC and FD12-15aa-HC were expressed and purified as the following: The plasmid was transformed into BL21(DE3). The expression was induced by adding 1 mM IPTG to the culture at OD600 of app. 1. The culture was grown for an additional 20 hours at 20° C., harvested and lysed by sonication in native lysis buffer (50 mM $NaH_2PO_4$, 300 mM NaCl, 10 mM imidazole pH 8.0).

The clarified bacterial lysate was brought to 50 ml with native lysis buffer. 5 ml nickel-nitrilotracetic acid (Ni-NTA) agarose (Qiagen) was added and the lysate was incubated by inverting for one hour at 4° C. Unspecifically bound proteins were removed by washing 4 times in native lysis buffer. Bound protein was eluted by resupension of the Ni-NTA agarose in 2 ml of elution buffer (50 mM $NaH_2PO_4$, 300 mM NaCl, 250 mM imidazole pH 8.0).

Example 5

Oxidative Folding Disulfide Bonds in Purified Fel D1 Fusion Proteins $Ni^{2+}$-affinity purified FELD1-HC consists of a variety of mixed-disulfide bridged species from 15 kD to 20 kD. Native folding of FELD1-HC was achieved by intramolecular reshuffling the disulfide bonds with oxidized glutathion (GSSG, Applichem) and reduced glutathion (GSH, Applichem) at a molar ratio of 1:1. The reaction was performed for 24 hours immediately after elution of FELD1 in the elution buffer by adding 2.5 mM GSSG and 2.5 mM GSH at room temperature. Refolded FELD1-HC showed a single band at a molecular weight of 15 kD under non-reducing condition (FIG. 1, the first panel, lane 2). The potential free sulfhydryl groups of FELD1-HC were alkylated using iodoacetamide (Sigma). Probes were treated with 5 mM iodoacctamide in 20 mM ammonium bicarbonate at pH 8.0 for 15 minutes at room temperature.

Refolded FELD1-HC was further purified to homogeneity by size-exclusion chromatography (SEC) (Superdex 75 pg, Amersham Pharmacia Biosciences) equilibrated in PBS.

FELD1-10aa-HC and FELD1-15aa-HC were renatured by substantially the same method as described above (FIG. 1, the two middle panels).

Native folding of FD12-15aa-HC was achieved similarly by reshuffling the disulfide bonds with oxidized glutathion and reduced glutathion at a molar ratio of 10:1. After elution FD12-15aa was twenty fold diluted in FD12-15aa refolding buffer (50 mM Tris-Cl pH 8.5, 240 mM NaCl, 10 mM KCl, 1 mM EDTA, 0.05% PEG 3,550, 1 mM GSH, 0.1 mM GSSH) and incubated at 4° C. for 24 hours. Refolded FD12-15aa showed a single band at a molecular weight of 20 kD compared to the reduced form running at 23 kD (FIG. 1, last panel).

Example 6

Fel d1 Fusion Proteins are Recognized by Epitope-Specific Monoclonal Antibodies

The binding of Fel d1 fusion proteins in comparison to natural Fel d1 (nFel d1) to epitope-specific monoclonal antibodies (mAB) was measured by a sandwich ELISA using the Fel d1 ELISA kit (6F9/3E4) from Indoor biotechnologies (Cardiff, UK).

Briefly, the anti-Fel d1 mAB 6F9 supplied as a 2 mg/ml stock solution was diluted 1:1000 in 50 mM carbonate-bicarbonite buffer pH 9.6. Microtiter wells were coated with 100 µl of the diluted mAB 6F9 per well at 4° C. overnight. Plates were washed three times with PBS-0.05% Tween20 (PBS-T) and then blocked with 100 µl blocking buffer (1% BSA (Sigma) in PBS-T). Then the microtiter wells were incubated for one hour with 100 µl of Fel d1 fusion proteins or nFel d1 standard (Indoors technologies; UK) using doubling dilutions from ng/ml. The nFel d1 reference was sub-standardized from the CBER cat dander reference E10, which contains 13.47 U/ml Fel d1 (1 unit=4 mg protein).

Plates were then washed and 100 µl diluted (1:1000 in 1% BSA/PBS-T) biotinylated anti-Fel d1 mAB 3E4 antibody was added and incubated for 1 h at room temperature. Plates were washed three times with PBS-T using 100 µl diluted (1:1000 in 1% BSA/PBS-T) Streptavidin-Peroxidase (Sigma S5512, 0.25 mg reconstituted in 1 ml destilled water). After 30 minutes incubation at room temperature wells were washed three times with PBS-T. Detection was performed with OPD substrate solution and 5% $H_2SO_4$ as stop solution. The absorbance was measured using ELISA reader (BioRad) at 450 nm and for calculation of arithmetic means and standard error of the mean (SEM) EXCEL software (MS Office; Microsoft) was used. The results are shown in TABLE 1. Thus the recognition of Fel d1 fusion proteins and nFel d1 by epitope-specific mABs reflects the high similarity of antigenicity of both proteins.

TABLE 1

|  | tested proteins | | | |
| --- | --- | --- | --- | --- |
|  | FELD1-HC | FELD1-10aa-HC | FELD1-15aa-HC | Nature Fel d1 |
| Fel d1 (ng/ml) at OD50% | 8.4 | 6.7 | 7.9 | 7.2 |

Example 7

Coupling of Fel d1 Fusion Proteins to VLPs Derived from Qβ

A solution of 143 µM Qβ VLP in HEPES buffer (20 mM HEPES, 150 mM NaCl, pH 7.2) was reacted with a 5-fold molar excess (715 µM) of SMPH (Pierce) for 30 minutes at 25° C. with shaking. SMPH was taken from a 50 mM stock dissolved in dimethyl sulfoxide. Reaction products were dialyzed against two changes of PBS using a dialysis unit with a 10,000 Da molecular weight cutoff (Slide-A-Lyzer, Pierce). Dialysis was performed at 4° C. at room temperature in a >1000-fold excess of buffer to reaction mixture.

Before coupling Fel d1 fusion proteins to SMPH-derivatized Qβ VLP, FELD1, FELD1-10aa, FELD1-15aa, and FD12-15aa, respectively, as obtained from EXAMPLE 5 was incubated with TCEP (Pierce, Perbio Science) in equimolar amounts for 30 minutes at room temperature.

Fel d1 fusion proteins was added in a 5-fold molar excess to a 143 µM solution of SMPH-derivatized Qβ VLPs. Reaction volume was 650 µl and multiple reactions were performed in parallel. Reactions were incubated for 4 hours at room temperature with shaking. After coupling, aliquots were centrifuged at 16,000×g for 3 minutes at 4° C. to pellet insoluble material. The supernatants were pooled in fresh tubes. The coupling of Fel d1 fusion proteins to Qβ VLP was assessed by reducing SDS-PAGE.

Coupling of Fel d1 fusion proteins to the reassembled Qβ VLP (obtained from EXAMPLE 1) is substantially the same as described above.

Example 8

Coupling FELD1, FELD1-15aa and FD12-15aa to HBcAg1-185-Lys

Construction of HBcAg1-185-Lys, its expression and purification have been substantially described in EXAMPLE 2-5 of WO 03/040164. A solution of 120 µM HBcAg1-185-Lys VLP in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed HBcAg1-185-Lys reaction mixture is then reacted with the recombinant Fel d1 obtained in EXAMPLE 5. In the coupling reaction the FELD1, FELD1-15aa and FD12-15aa, respectively, is in twofold molar excess over the derivatized HBcAg1-185-Lys VLP. The coupling reaction proceeds for four hours at 25° C. on a rocking shaker.

Example 9

Coupling of FELD1, FELD1-15aa and FD12-15aa to VLPs Derived from AP205

The preparation of AP205 VLP was described in EXAMPLE 1 and 2 in WO 2004/007538. The derivatization of AP205 VLP is substantially the same as described in EXAMPLE 7 for Qβ VLP. Before coupling Fel d1 fusion proteins to SMPH-derivatized AP205 VLP, FELD1, FELD1-15aa and FD12-15aa obtained from EXAMPLE 5, respectively, is incubated with TCEP (Pierce, Perbio Science) in equimolar amounts for 30 minutes at room temperature.

Fel d1 fusion proteins is added in a 5-fold molar excess to the 143 µM solution of SMPH-derivatized AP205 VLPs. Reactions are incubated for 4 hours at room temperature with shaking.

Coupling of Fel d1 fusion proteins to the reassembled AP205 VLP (obtained from EXAMPLE 2) is substantially the same as described above.

Example 10

Production of Bacteriophage Qβ Based Inventive Composition

A 60 l culture of E. coli AB259 ($5 \times 10^7$ cells/ml) was grown for 2-3 hours at 37° C. under intensive aeration (1 volume of air/volume of culture-minute) to obtain a culture of about 2-4×10⁹ cells/ml. Clarified Qβ phage lysate was inoculated at a multiplicity of infection of 5, and CaCl$_2$ was added to a final concentration of 2.2 mM. After an adsorption phase of 5 minutes, aeration was intensified (1.5 volumes of air/volume of culture-minute) The cells were further grown for 3 hours, until OD$_{650\ nm}$ reached a stable value, yielding 4-6×10¹² phage particles in the culture. These were purified as follows. E. coli was lysed by adding 10 ml CHCl$_3$/1 culture, 0.1 mg Lysozyme/1 culture and EDTA to a final concentration of 20 mM. The lysate was clarified by centrifigation in a cooled flow-through centrifuge, the phage particles sedimented from the lysate by ammonium sulphate precipitation (500 g/l, yielding approx. 66% saturation). The suspension was first decanted, and the precipitate isolated by centrifugation for 30 minutes using a Janetzki K26 centrifuge with W.R. rotor 6×500 ml at 6000 rpm, or in a Beckman J21 C centrifuge using a JA-10 rotor. The pellet was resolubilized in NT buffer (0.15 M NaCl, 0.1% Trypton) and clarified by centrifugation. The supernatant was precipitated with ammonium sulphate (500 g/l added, approx. 66% saturation). The precipitate was isolated by centrifugation, resolubilized in NT buffer and clarified again by centrifugation. The phage particles were isolated from the resulting supernatant by ultracentrifugation for 3.5 h, using a Beckman type 35 rotor at 32 000 rpm. The sedimented phages were resuspended in NT buffer and purified by ultracentrifugation over a conventional continuous CsCl gradient. Centrifugation was performed using a Beckman Ti-70 (8×38.5) rotor, at 55 000 rpm for 20 hours. The phage particles were subsequently dialyzed against 20 mM Hepes, 150 mM NaCl, pH 7.4 buffer to be used in chemical cross-linking steps as described in EXAMPLE 7.

Example 11

Preparation of GA Phage Based Inventive Composition

A culture of 121 E. coli Q 13 Hfr RNASse I⁻ culture in M9 medium containing 2% casein hydrolysate, 0.5% Yeast extract, 0.2% glucose was grown to an OD$_{540\ nm}$ of 0.6-0.7, which corresponds to approx. to 2×10⁸ cells/ml, and infected with GA phage at a multiplicity of infection of 10-20. The culture was grown for further 2.5-3 hours at 37° C. yielding approx. 10¹¹ phage particles in the total culture. The cells were lysed by adding 1-2% v/v of CHCl$_3$ and incubating the culture for 15 minutes. The lysate was clarified by centrifugation for 30 minutes at 5000 rpm on a Janetzki K26 rotor. The phage particles were precipitated with ammonium sulphate (60% saturation) from the culture media during several days at 4° C. The suspension was first decanted, and the precipitate isolated by centrifugation for 30 minutes at 6000 rpm in a Janetzki K26 rotor. The pellet was resuspended in NET (20 mM Tris pH7.8, 150 mM NaCl, 5 mM EDTA) buffer, and the particles extracted by several cycles of centrifugation and resuspension in small portions of NET buffer. The portions containing capsids were pooled, and precipitated with 60% ammonium sulphate. The particles resuspended in NET buffer were purified three times over a Sepharose 4B column, and subsequently over two sucrose gradients. Briefly, a gradient was prepared with 7 ml of 50%, 7 ml of 43%, 7 ml of 36%, 7 ml of 29% and 7 ml of 22% w/w sucrose in NET buffer in centrifugal tubes. The phage solution (in NET buffer) was layered on the gradient, and centrifuged for 17 h in a Beckman SW 28 rotor at 25 000 rpm. The fractions containing capsids were pooled, and separated from sucrose by gel filtration over a Sepharose 4B column. The phage particles were subsequently dialyzed against water and lyophilized for further use.

The condition of coupling of Fel d1 fusion proteins to the bacteriophage Qβ or GA is substantially the same as the coupling condition to the VLP of Qβ as disclosed in EXAMPLE 7.

Example 12

Qβ-Fel d1 Fusion Proteins are Highly Immunogenic in Mice

BALB/c mice were immunized sc with 50 ug of Qβ-FELD1 obtained from EXAMPLE 7 or 50 ug of Qβ mixed with recombinant Fel d1 (obtained from EXAMPLE 5) on days 0, 14 and 21 and blood was taken on days 0, 21 and 28. Fel d1 specific antibodies were measured by ELISA using FELD1 for coating (10 ug/ml). In brief, 96-well F96 that were pre-coated at 4° C. overnight with 10 μg/ml FELD1 in 0.1 M NaHCO3 pH 9.6 were used. Plates were washed four times with PBS-Tween20 and background was reduced by incubating the plates 2 h at 37° C. in blocking buffer (2% BSA, (Sigma) in PBS-Tween20). The serum was diluted in serum dilution buffer (2% BSA, 1% FCS in PBS-Tween20). Two-fold dilution steps were done and incubated for 2 h at room temperature on ELISA plate shaker. Plates were washed five times and 1:1000 diluted detection antibody (anti-mouse IgG HRPO coupled (Sigma)) was incubated for 1 h at room temperature. Plates were washed five times with PBS-Tween20 and detection was performed using OPD substrate solution (0.066 M Na$_2$HPO$_4$, 0.035 M citric acid pH5.0 containing 10 mg OPD (Fluka) and 8 μl of 30% H$_2$O$_2$ (Fluka) per 25 ml) and 5% H$_2$SO$_4$ in H$_2$O as stop solution. The absorbance was measured using ELISA reader at 450 nm and for calculation of arithmetic means and standard error of the mean (SEM) EXCEL software (Microsoft) was used.

Qβ-FELD1 immunized mice showed a halfmaximal absorption of 120,000 and 75,000 at day 21 and day 28, respectively. In contrast mice immunized with a non-cross linked Qβ/FELD 1 mixture had a low titer of 7000 and 6000 at day 21 day 28, respectively.

Example 13

Immunization of Mice with Alum as Adjuvant 7-8 week old female Balb/c mice were vaccinated three times (day 0, 14 and 28) with 50 μg the prior art QβVLP-FELD1-HC. The vaccines were diluted in 200 ul of sterile PBS or 100 μl PBS and 100 μl AluGel-S (Serva), respectively, and injected subcutaneously into the left and right inguinal region.

Sera were collected at day 14, 21, 28, 42, 56, 84 and 112. Antibodies specific against the natural Fel d1, FELD1-HC and QB VLP were determined by ELISA.

Microtiter plates were coated overnight with 1 μg/ml natural Fel d1 (nFel d1, Indoors biotechnologies), 10 mg/ml FELD1-HC and 10 mg/ml Qb VLP, respectively. After washing (0.05% Tween 20/PBS) and blocking with 2% BSA in PBS, sera were added at different dilutions in 2% BSA/1% FCS/PBS.

Thereafter the ELISA was carried out by standard method. Qβ VLP-FELD1-HC vaccines induced a long-lasting high Feld1-specific antibody response towards natural and FELD1. The antibody titer was higher in the presence of Alum than without Alum (TABLE 2).

TABLE 2

| dates | with Alum | | without Alum | |
|---|---|---|---|---|
| | nFel d1 | FELD1-HC | nFel d1 | FELD1-HC |
| Day 13 | 15984 | 53939 | 3394 | 7871 |
| Day 20 | 100311 | 203636 | 38980 | 77323 |
| Day 27 | 173190 | 368716 | 38177 | 56836 |
| Day 42 | 240173 | 419072 | 88953 | 170377 |
| Day 56 | 228500 | 492520 | 65370 | 163093 |
| Day 84 | 157009 | 219834 | 59603 | 115049 |
| Day 112 | 127745 | 203719 | 62290 | 116132 |

Example 14

FELD1 Coupled to Qβ has Drastically Reduced Allergic Potential In Vitro

To test the ability of Qβ-FELD1-HC to trigger an allergic reaction in vitro, basophils were isolated from the blood of three cat allergic donors. In a cat allergic individual, these basophils are coated with Fel d1 specific IgE and respond with the upregulation of CD63 to allergenic stimulation. Thus, basophils of the allergic individual were stimulated with graded amounts of Qβ-FELD1-HC or FELD1-HC alone and upregulation of CD63 was assessed by flow cytometry. While FELD1-HC (obtained from EXAMPLE 5) triggered strong upregulation of CD63 at the lowest dilution tested (about 0.2 ng/ml), Qβ-FELD1-HC (obtained from EXAMPLE 7) exhibited a drastically reduced allergic potential and required 100-1000 fold higher amounts (about 70 ng/ml) of FELD1-HC for the basophiles to respond.

Figure 2:
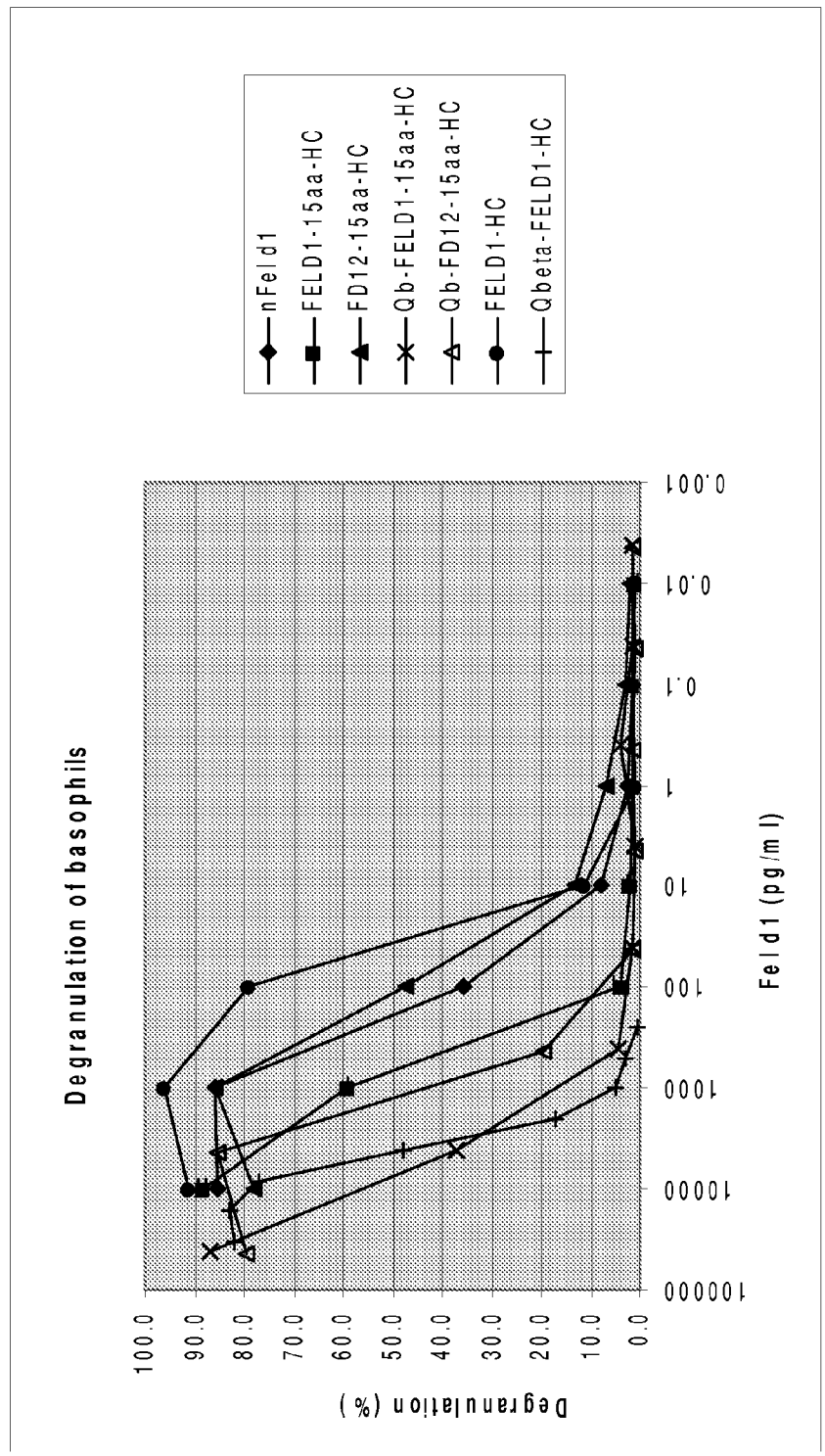

Similarly this test was repeated for the fusion proteins FELD-15aa-HC, and FD12-15aa-HC either alone or coupled to Qβ. The results are shown in FIG. 2. These Fel d1 fusion proteins, when coupled to Qβ, all exhibited a drastically reduced allergic potential.

Example 15

FELD1 Coupled to Qβ is Unable to Trigger a Skin-Prick Reaction in an Allergic Individual If allergens are introduced by pricking into the skin of an allergic individual, a local edema is generated within about 20 minutes due to activation of mast cells resident in the skin. Here, the skin test was employed to determine the allergic potential of Q-FELD1-HC (obtained from EXAMPLE 7). Graded amounts of Qβ-FELD1-HC or corresponding amounts of FELD1-HC (obtained from EXAMPLE 5) were introduced into the skin of a cat allergic individual and the skin reaction was assessed 20 minutes later. Qβ-FELD1-HC was unable to trigger a skin reaction while FELD1-HC was active at more than 100 fold lower concentrations (TABLE 3)

TABLE 3

Corresponding amounts of FELD1-HC were present in both preparations.

| Dilution | FELD1-HC | Qβ-FELD1-HC |
|---|---|---|
| Neat | +++ | − |
| 1:10 | ++ | − |
| 1:100 | + | − |
| 1:1000 | − | − |

Example 16

Figure 3:
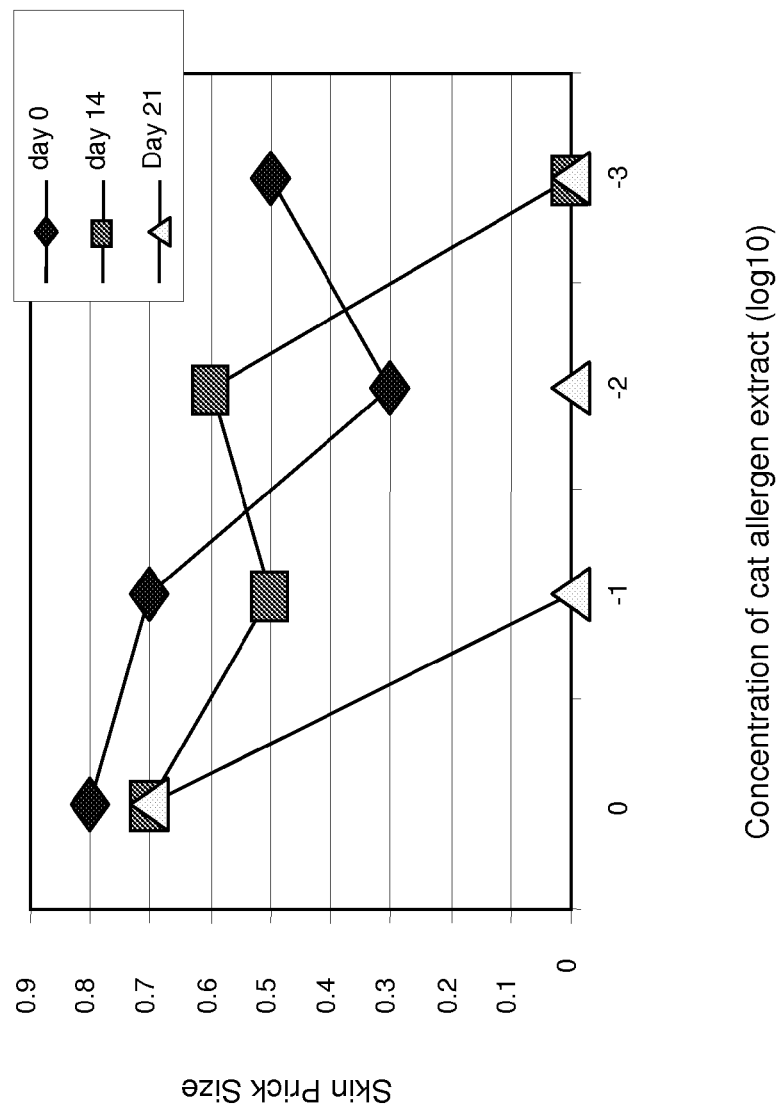

Immunization of an Allergic Individual with Qβ-FELD-HC Reduces Skin Prick Test Reactivity In order to test the ability of Qβ-FELD-HC to ameliorate clinical symptoms, a patient suffering from cat allergy was vaccinated with 17 ug Qβ-FELD1-HC (obtained from EXAMPLE 7) on day 0 (3 injections of 2, 5 and 10 ug), 40 ug on day 7 (3 injections of 10, 10 and 20 ug) and 50 ug on day 14 (2 injections of 10 and 40 ug). Skin prick testes were performed with a standardized cat extract on days 0, 14 and 21 and the diameters of the central swelling reaction was quantified (FIG. 3). Within 3 weeks, 1000-fold higher allergen concentrations were required to induce clinical symptoms in the skin prick test than the initial amount sufficient to induce symptom in the prick test.

Example 17

Figure 4A:
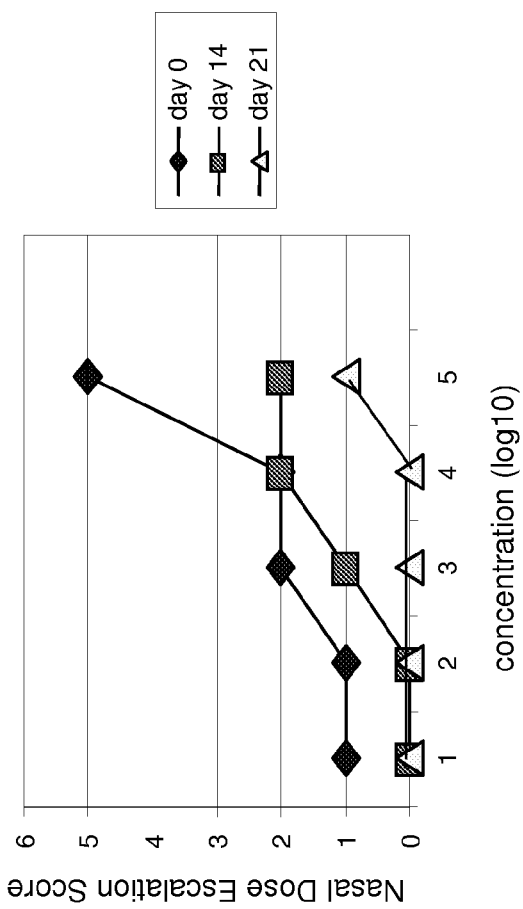
Figure 4B:
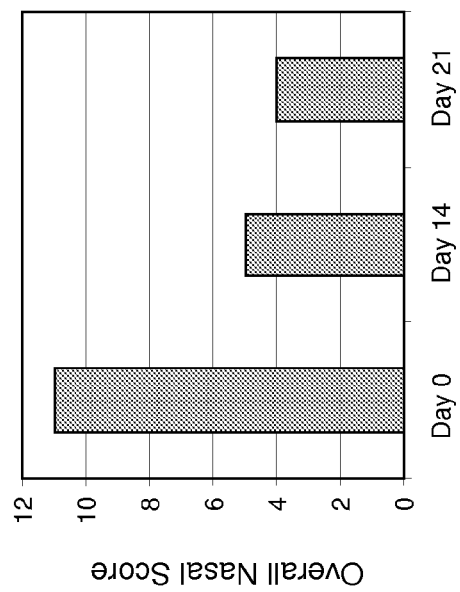

Immunization of an Allergic Individual with Qβ-FELD1-HC Reduces Allergic Symptoms in Nasal Provocation Test In order to test the ability of Qβ-FELD1-HC to ameliorate clinical symptoms, a patient suffering from cat allergy was vaccinated with 17 ug Qβ-FELD1-HC (obtained from EXAMPLE 7) on day 0 (3 injections of 2, 5 and 10 ug), 40 ug on day 7 (3 injections of 10, 10 and 20 ug) and 50 ug on day 14 (2 injections of 10 and 40 ug). Nasal provocation tests were performed with a standardized cat extract on days 0, 14 and 21 and the clinical symptoms were assessed at each dose escalation level (FIG. 4A) and an overall allergic rating was made according to (FIG. 4B). Within 3 weeks, 100-1000-fold higher allergen concentrations were required to induce clinical symptoms and the overall allergic rating was strongly reduced.

Example 18

Packaging Immunosimulatory Nucleic Acids into Qβ VLP

Disassembled and purified coat protein of Qβ was obtained as described in EXAMPLE 1 (A) and (B). Reassembly: β-mercaptoethanol was added to the 10 ml dimer fraction to a final concentration of 10%, and 300 µl of a solution of $(CpG)_{20}OpA$ oligodeoxynucleotide, containing 12.3 mmol of oligonucleotide, were added. The reassembly mixture was first dialyzed against 30 ml NET buffer (20 mM Tris-HCl, pH 7.8 with 5 mM EDTA and 150 mM NaCl) containing 10% beta-mercaptoethanol for 2 hours at 4° C., and then dialyzed in a continuous mode, with a flow of NET buffer of 8 ml/h over 4 days at 4° C. The reassembly mixture was then desalted against water by dialysis, with 6 buffer exchanges (4×100 ml, 2×1 liter).

Coupling Fel d1 fusion proteins to the Qβ VLP with packaged CpG inside is carried out substantially the same as described in EXAMPLE 7.

Example 19

Fel d1 Specific Serum Inhibited the Fel d1 Fusion Proteins Induced Basophil Degranulation In Vitro To test the ability of anti-Fel d1 specific IgG to inhibit degranulation, basophils of an allergic individual were stimulated with a defined amount of FELD1-HC or FELD1-15aa-HC pre-incubated with a serial of dilutions of decreasing amounts of IgGs isolated from Q-FELD1-HC immunized rabbits. Upregulation of CD63 was assessed by flow cytometry. Anti-Fel d1 IgG blocked the Fel d1-induced degranulation at all tested concentrations while control IgG did not show any effect (TABLE 4).

TABLE 4

| | samples | |
|---|---|---|
| | FELD1-HC Percentage of degranulation | FELD1-15aa-HC Percentage of degranulation |
| No IgG | 33 | 33 |
| Fel d1 specific IgG (200 ng/ml) | 1.9 | 1.6 |
| Fel d1 specific IgG (100 ng/ml) | 5.2 | 2.1 |
| Fel d1 specific IgG (50 ng/ml) | 8.2 | 2.3 |
| Fel d1 specific IgG (25 ng/ml) | 10.6 | 4.2 |
| Unspecific IgG | 35 | 29 |
| No Fel d1 stimulation | 1.2 | 1.2 |

Example 20

Immunization of Fel d1 Allergic Mice with Qβ-FELD1-HC

An experimental asthma model of allergic airway inflammation in mice was used to assess the effects of vaccination against the natural allergen Fel d1 on the IgE antibody response in serum and BAL (Bronchoalveolar lavage) of BALB/c mice. 5 mice per group were peritoneally sensitized with 1 ug natural Fel d1 in AlumGel-S at day 0. Mice were subcutaneously vaccinated on day 35 and 49 with either 50 ug Qβ alone or with 50 ug Qβ-FELD1-HC before two subsequent intranasal challenges on day 63 and day 70. 5 days after the last intranasal challenge, mice were sacrificed to collect serum and BALF (Bronchoaleveolar Lavage Fluid) for analysis of the humoral immune response (IgE subclass titers) by ELISA.

ELISA plates were coated with a rat anti-IgE mAb (2 ug/ml) diluted in Carbonat buffer over night at 4° C. After blocking of plated with PBS/5% BSA for 2 hours, plates were incubated for further two hours with either serum (first well 1:100 pre-diluted, then 1:3 dilution over 8 steps) or BAL (first well pure BAL then 1:3 dilution over 8 steps) of sensitized, vaccinated and antigen-challenged mice. After 2 hours of sample incubation, serum and BAL-IgE was detected with a rat anti-mouse IgE-HRP labelled antibody prior detection with the substrate OPD.

TABLE 5

| | Serum (d75) | | BAL (d75) | |
|---|---|---|---|---|
| Group | Titer at OD50 | % reduction | Titer at OD50 | % reduction |
| Qβ-vaccinated | 1036 | — | 15 | — |
| Qβ-Fel d1 vaccinated | 49 | 95 | 0 | 100 |

What is claimed is:

1. A composition comprising:
   (a) a core particle with at least one first attachment site, wherein said core particle is a virus-like particle (VLP) of an RNA-bacteriophage,
   (b) at least one antigen with at least one second attachment site,
   wherein said at least one antigen is a Fel d1 protein, wherein said Fel d1 protein is a fusion protein comprising chain 1 of Fel d1 and chain 2 of Fel d1, wherein said chain 2 of Fel d1 is fused via its C-terminus to the N-terminus of said chain 1 of Fel d1 via a spacer consisting of an amino acid sequence having 10-20 amino acid residues, and
   wherein (a) and (b) are covalently linked through said at least one first and said at least one second attachment site.

2. The composition of claim 1, wherein said chain 1 of Fel d 1 comprises a sequence of SEQ ID NO: 22 or a homologue sequence thereof, wherein said homologue sequence has an identity to SEQ ID NO: 22 of greater than 95%.

3. The composition of claim 1, wherein said chain 2 of Fel d 1 comprises a sequence of SEQ ID NO: 23, SEQ ID NO: 25 or SEQ ID NO: 26, or a homologue sequence thereof, wherein said homologue sequence has an identity to SEQ ID NO: 23, SEQ ID NO: 25 or SEQ ID NO: 26 of greater than 95%.

4. The composition of claim 1, wherein said first attachment site comprises an amino group.

5. The composition of claim 1, wherein said second attachment site comprises a sulfhydryl group.

6. The composition of claim 1 further comprising a linker, wherein said linker is fused to the C-terminus of said Fel d1 protein, and wherein said linker comprises said second attachment site and comprises a cysteine residue.

7. The composition of claim 1 further comprising at least one adjuvant.

8. A pharmaceutical composition comprising:
   (a) the composition of claim 1; and
   (b) an acceptable pharmaceutical carrier.

9. A method of producing the composition of claim 1 comprising:
   (a) providing a core particle with at least one first attachment site, wherein said core particle is a virus-like particle (VLP) of an RNA-bacteriophage;
   (b) providing at least one antigen with at least one second attachment site, wherein said antigen is a Fel d1 protein, wherein said Fel d1 protein is a fusion protein comprising chain 1 of Fel d1 and chain 2 of Fel d1, wherein said chain 2 of Fel d1 is fused via its C-terminus to the N-terminus of said chain 1 of Fel d1 via a spacer consisting of an amino acid sequence having 10-20 amino acid residues; and
   (c) linking said core particle and said at least one antigen to produce said composition, wherein said at least one antigen and said core particle are linked through said at least one first and said at least one second attachment sites.

10. A method of treating cat allergy comprising administering the composition of claim 1 to a human or to a non-human mammal.

11. The composition of claim 1, wherein said RNA-bacteriophage is AP205.

12. The composition of claim 4, wherein said amino group is an amino group of a lysine.

13. The composition of claim 5, wherein said sulfhydryl group is a sulfhydryl group of a cysteine.

14. The composition of claim 1, wherein said fusion protein comprises the amino acid sequence as set forth in SEQ ID NO:54.

15. The composition of claim 1, wherein said fusion protein comprises the amino acid sequence as set forth in SEQ ID NO:55.

16. The composition of claim 1, wherein said core particle is a VLP of RNA-bacteriophage Qβ.

17. The composition of claim 16, wherein said VLP of RNA-bacteriophage Qβ comprises one or more recombinant proteins consisting of the amino acid sequence as set forth in SEQ ID NO:1.

18. The composition of claim 1, wherein said first attachment site is linked to said second attachment site via at least one non-peptide covalent bond.

19. The composition of claim 18, wherein said first attachment site comprises an amino group of a lysine and said second attachment site comprises a sulfhydryl group of a cysteine.

20. The composition of claim 16, wherein said core particle is a VLP of RNA-bacteriophage Qβ comprising one or more recombinant proteins consisting of the amino acid sequence as set forth in SEQ ID NO:1.

21. The composition of claim 20, wherein said first attachment site is linked to said second attachment site via at least one non-peptide covalent bond.

22. The composition of claim 21, wherein said first attachment site comprises an amino group of a lysine and said second attachment site comprises a sulfhydryl group of a cysteine.

23. The composition of claim 22 further comprising a hetero-bifunctional cross-linker, wherein said heterobifunctional cross-linker is SMPH.

* * * * *

SEQUENCE LISTING

<160> NUMBER OF SEQ ID NOS: 69

<210> SEQ ID NO 1
<211> LENGTH: 132
<212> TYPE: PRT
<213> ORGANISM: Bacteriophage Q-beta

<400> SEQUENCE: 1

Ala Lys Leu Glu Thr Val Thr Leu Gly Asn Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Ala Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

```
<210> SEQ ID NO 2
<211> LENGTH: 329
<212> TYPE: PRT
<213> ORGANISM: Bacteriophage Q-beta

<400> SEQUENCE: 2
```

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr Trp Thr Leu Leu Ile Ala Gly Gly Gly Ser Gly
    130                 135                 140

Ser Lys Pro Asp Pro Val Ile Pro Asp Pro Pro Ile Asp Pro Pro Pro
145                 150                 155                 160

Gly Thr Gly Lys Tyr Thr Cys Pro Phe Ala Ile Trp Ser Leu Glu Glu
                165                 170                 175

Val Tyr Glu Pro Pro Thr Lys Asn Arg Pro Trp Pro Ile Tyr Asn Ala
            180                 185                 190

Val Glu Leu Gln Pro Arg Glu Phe Asp Val Ala Leu Lys Asp Leu Leu
        195                 200                 205

Gly Asn Thr Lys Trp Arg Asp Trp Asp Ser Arg Leu Ser Tyr Thr Thr
    210                 215                 220

Phe Arg Gly Cys Arg Gly Asn Gly Tyr Ile Asp Leu Asp Ala Thr Tyr
225                 230                 235                 240

Leu Ala Thr Asp Gln Ala Met Arg Asp Gln Lys Tyr Asp Ile Arg Glu
                245                 250                 255

Gly Lys Lys Pro Gly Ala Phe Gly Asn Ile Glu Arg Phe Ile Tyr Leu
            260                 265                 270

Lys Ser Ile Asn Ala Tyr Cys Ser Leu Ser Asp Ile Ala Ala Tyr His
        275                 280                 285

Ala Asp Gly Val Ile Val Gly Phe Trp Arg Asp Pro Ser Ser Gly Gly
    290                 295                 300

Ala Ile Pro Phe Asp Phe Thr Lys Phe Asp Lys Thr Lys Cys Pro Ile
305                 310                 315                 320

Gln Ala Val Ile Val Val Pro Arg Ala
                325

```
<210> SEQ ID NO 3
<211> LENGTH: 129
<212> TYPE: PRT
<213> ORGANISM: Bacteriophage R17

<400> SEQUENCE: 3
```

Ala Ser Asn Phe Thr Gln Phe Val Leu Val Asn Asp Gly Gly Thr Gly

```
                           1               5                  10                 15

Asn Val Thr Val Ala Pro Ser Asn Phe Ala Asn Gly Val Ala Glu Trp
                 20                  25                 30

Ile Ser Ser Asn Ser Arg Ser Gln Ala Tyr Lys Val Thr Cys Ser Val
         35                  40                  45

Arg Gln Ser Ser Ala Gln Asn Arg Lys Tyr Thr Ile Lys Val Glu Val
         50                  55                  60

Pro Lys Val Ala Thr Gln Thr Val Gly Gly Val Glu Leu Pro Val Ala
65                   70                  75                  80

Ala Trp Arg Ser Tyr Leu Asn Met Glu Leu Thr Ile Pro Ile Phe Ala
             85                  90                  95

Thr Asn Ser Asp Cys Glu Leu Ile Val Lys Ala Met Gln Gly Leu Leu
                 100                 105                 110

Lys Asp Gly Asn Pro Ile Pro Ser Ala Ile Ala Ala Asn Ser Gly Ile
             115                 120                 125

Tyr

<210> SEQ ID NO 4
<211> LENGTH: 130
<212> TYPE: PRT
<213> ORGANISM: Bacteriophage fr

<400> SEQUENCE: 4

Met Ala Ser Asn Phe Glu Glu Phe Val Leu Val Asp Asn Gly Gly Thr
1               5                   10                  15

Gly Asp Val Lys Val Ala Pro Ser Asn Phe Ala Asn Gly Val Ala Glu
                 20                  25                 30

Trp Ile Ser Ser Asn Ser Arg Ser Gln Ala Tyr Lys Val Thr Cys Ser
             35                  40                  45

Val Arg Gln Ser Ser Ala Asn Asn Arg Lys Tyr Thr Val Lys Val Glu
         50                  55                  60

Val Pro Lys Val Ala Thr Gln Val Gln Gly Gly Val Glu Leu Pro Val
65                   70                  75                  80

Ala Ala Trp Arg Ser Tyr Met Asn Met Glu Leu Thr Ile Pro Val Phe
             85                  90                  95

Ala Thr Asn Asp Asp Cys Ala Leu Ile Val Lys Ala Leu Gln Gly Thr
                 100                 105                 110

Phe Lys Thr Gly Asn Pro Ile Ala Thr Ala Ile Ala Ala Asn Ser Gly
         115                 120                 125

Ile Tyr
    130

<210> SEQ ID NO 5
<211> LENGTH: 130
<212> TYPE: PRT
<213> ORGANISM: Bacteriophage GA

<400> SEQUENCE: 5

Met Ala Thr Leu Arg Ser Phe Val Leu Val Asp Asn Gly Gly Thr Gly
1               5                   10                  15

Asn Val Thr Val Val Pro Val Ser Asn Ala Asn Gly Val Ala Glu Trp
                 20                  25                 30

Leu Ser Asn Asn Ser Arg Ser Gln Ala Tyr Arg Val Thr Ala Ser Tyr
             35                  40                  45

Arg Ala Ser Gly Ala Asp Lys Arg Lys Tyr Ala Ile Lys Leu Glu Val
         50                  55                  60
```

```
Pro Lys Ile Val Thr Gln Val Val Asn Gly Val Glu Leu Pro Gly Ser
 65                  70                  75                  80

Ala Trp Lys Ala Tyr Ala Ser Ile Asp Leu Thr Ile Pro Ile Phe Ala
                 85                  90                  95

Ala Thr Asp Asp Val Thr Val Ile Ser Lys Ser Leu Ala Gly Leu Phe
            100                 105                 110

Lys Val Gly Asn Pro Ile Ala Glu Ala Ile Ser Ser Gln Ser Gly Phe
        115                 120                 125

Tyr Ala
    130

<210> SEQ ID NO 6
<211> LENGTH: 132
<212> TYPE: PRT
<213> ORGANISM: Bacteriophage SP

<400> SEQUENCE: 6

Met Ala Lys Leu Asn Gln Val Thr Leu Ser Lys Ile Gly Lys Asn Gly
 1               5                  10                  15

Asp Gln Thr Leu Thr Leu Thr Pro Arg Gly Val Asn Pro Thr Asn Gly
             20                  25                  30

Val Ala Ser Leu Ser Glu Ala Gly Ala Val Pro Ala Leu Glu Lys Arg
         35                  40                  45

Val Thr Val Ser Val Ala Gln Pro Ser Arg Asn Arg Lys Asn Phe Lys
     50                  55                  60

Val Gln Ile Lys Leu Gln Asn Pro Thr Ala Cys Thr Arg Asp Ala Cys
 65                  70                  75                  80

Asp Pro Ser Val Thr Arg Ser Ala Phe Ala Asp Val Thr Leu Ser Phe
                 85                  90                  95

Thr Ser Tyr Ser Thr Asp Glu Glu Arg Ala Leu Ile Arg Thr Glu Leu
            100                 105                 110

Ala Ala Leu Leu Ala Asp Pro Leu Ile Val Asp Ala Ile Asp Asn Leu
        115                 120                 125

Asn Pro Ala Tyr
    130

<210> SEQ ID NO 7
<211> LENGTH: 329
<212> TYPE: PRT
<213> ORGANISM: Bacteriophage SP

<400> SEQUENCE: 7

Ala Lys Leu Asn Gln Val Thr Leu Ser Lys Ile Gly Lys Asn Gly Asp
 1               5                  10                  15

Gln Thr Leu Thr Leu Thr Pro Arg Gly Val Asn Pro Thr Asn Gly Val
             20                  25                  30

Ala Ser Leu Ser Glu Ala Gly Ala Val Pro Ala Leu Glu Lys Arg Val
         35                  40                  45

Thr Val Ser Val Ala Gln Pro Ser Arg Asn Arg Lys Asn Phe Lys Val
     50                  55                  60

Gln Ile Lys Leu Gln Asn Pro Thr Ala Cys Thr Arg Asp Ala Cys Asp
 65                  70                  75                  80

Pro Ser Val Thr Arg Ser Ala Phe Ala Asp Val Thr Leu Ser Phe Thr
                 85                  90                  95

Ser Tyr Ser Thr Asp Glu Glu Arg Ala Leu Ile Arg Thr Glu Leu Ala
            100                 105                 110
```

```
Ala Leu Leu Ala Asp Pro Leu Ile Val Asp Ala Ile Asp Asn Leu Asn
            115                 120                 125

Pro Ala Tyr Trp Ala Leu Leu Val Ala Ser Ser Gly Gly Asp
130                 135                 140

Asn Pro Ser Asp Pro Asp Val Pro Val Val Pro Asp Val Lys Pro Pro
145                 150                 155                 160

Asp Gly Thr Gly Arg Tyr Lys Cys Pro Phe Ala Cys Tyr Arg Leu Gly
                165                 170                 175

Ser Ile Tyr Glu Val Gly Lys Glu Gly Ser Pro Asp Ile Tyr Glu Arg
            180                 185                 190

Gly Asp Glu Val Ser Val Thr Phe Asp Tyr Ala Leu Glu Asp Phe Leu
        195                 200                 205

Gly Asn Thr Asn Trp Arg Asn Trp Asp Gln Arg Leu Ser Asp Tyr Asp
        210                 215                 220

Ile Ala Asn Arg Arg Cys Arg Gly Asn Gly Tyr Ile Asp Leu Asp
225                 230                 235                 240

Ala Thr Ala Met Gln Ser Asp Asp Phe Val Leu Ser Gly Arg Tyr Gly
                245                 250                 255

Val Arg Lys Val Lys Phe Pro Gly Ala Phe Gly Ser Ile Lys Tyr Leu
            260                 265                 270

Leu Asn Ile Gln Gly Asp Ala Trp Leu Asp Leu Ser Glu Val Thr Ala
        275                 280                 285

Tyr Arg Ser Tyr Gly Met Val Ile Gly Phe Trp Thr Asp Ser Lys Ser
    290                 295                 300

Pro Gln Leu Pro Thr Asp Phe Thr Gln Phe Asn Ser Ala Asn Cys Pro
305                 310                 315                 320

Val Gln Thr Val Ile Ile Pro Ser
                325

<210> SEQ ID NO 8
<211> LENGTH: 130
<212> TYPE: PRT
<213> ORGANISM: Bacteriophage MS2

<400> SEQUENCE: 8

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
130
```

<210> SEQ ID NO 9
<211> LENGTH: 133
<212> TYPE: PRT
<213> ORGANISM: Bacteriophage M11

<400> SEQUENCE: 9

Met Ala Lys Leu Gln Ala Ile Thr Leu Ser Gly Ile Gly Lys Lys Gly
1               5                   10                  15

Asp Val Thr Leu Asp Leu Asn Pro Arg Gly Val Asn Pro Thr Asn Gly
            20                  25                  30

Val Ala Ala Leu Ser Glu Ala Gly Ala Val Pro Ala Leu Glu Lys Arg
        35                  40                  45

Val Thr Ile Ser Val Ser Gln Pro Ser Arg Asn Arg Lys Asn Tyr Lys
    50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ser Asp Val Thr Phe Ser
                85                  90                  95

Phe Thr Gln Tyr Ser Thr Val Glu Glu Arg Ala Leu Val Arg Thr Glu
            100                 105                 110

Leu Gln Ala Leu Leu Ala Asp Pro Met Leu Val Asn Ala Ile Asp Asn
        115                 120                 125

Leu Asn Pro Ala Tyr
    130

<210> SEQ ID NO 10
<211> LENGTH: 133
<212> TYPE: PRT
<213> ORGANISM: Bacteriophage MX1

<400> SEQUENCE: 10

Met Ala Lys Leu Gln Ala Ile Thr Leu Ser Gly Ile Gly Lys Asn Gly
1               5                   10                  15

Asp Val Thr Leu Asn Leu Asn Pro Arg Gly Val Asn Pro Thr Asn Gly
            20                  25                  30

Val Ala Ala Leu Ser Glu Ala Gly Ala Val Pro Ala Leu Glu Lys Arg
        35                  40                  45

Val Thr Ile Ser Val Ser Gln Pro Ser Arg Asn Arg Lys Asn Tyr Lys
    50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ala Asp Val Thr Phe Ser
                85                  90                  95

Phe Thr Gln Tyr Ser Thr Asp Glu Glu Arg Ala Leu Val Arg Thr Glu
            100                 105                 110

Leu Lys Ala Leu Leu Ala Asp Pro Met Leu Ile Asp Ala Ile Asp Asn
        115                 120                 125

Leu Asn Pro Ala Tyr
    130

<210> SEQ ID NO 11
<211> LENGTH: 330
<212> TYPE: PRT
<213> ORGANISM: Bacteriophage NL95

<400> SEQUENCE: 11

Met Ala Lys Leu Asn Lys Val Thr Leu Thr Gly Ile Gly Lys Ala Gly
1               5                   10                  15

```
Asn Gln Thr Leu Thr Leu Thr Pro Arg Gly Val Asn Pro Thr Asn Gly
                20                  25                  30

Val Ala Ser Leu Ser Glu Ala Gly Ala Val Pro Ala Leu Glu Lys Arg
            35                  40                  45

Val Thr Val Ser Val Ala Gln Pro Ser Arg Asn Arg Lys Asn Tyr Lys
        50                  55                  60

Val Gln Ile Lys Leu Gln Asn Pro Thr Ala Cys Thr Lys Asp Ala Cys
65                  70                  75                  80

Asp Pro Ser Val Thr Arg Ser Gly Ser Arg Asp Val Thr Leu Ser Phe
                85                  90                  95

Thr Ser Tyr Ser Thr Glu Arg Glu Arg Ala Leu Ile Arg Thr Glu Leu
            100                 105                 110

Ala Ala Leu Leu Lys Asp Asp Leu Ile Val Asp Ala Ile Asp Asn Leu
        115                 120                 125

Asn Pro Ala Tyr Trp Ala Ala Leu Leu Ala Ala Ser Pro Gly Gly Gly
                130                 135                 140

Asn Asn Pro Tyr Pro Gly Val Pro Asp Ser Pro Asn Val Lys Pro Pro
145                 150                 155                 160

Gly Gly Thr Gly Thr Tyr Arg Cys Pro Phe Ala Cys Tyr Arg Arg Gly
                165                 170                 175

Glu Leu Ile Thr Glu Ala Lys Asp Gly Ala Cys Ala Leu Tyr Ala Cys
            180                 185                 190

Gly Ser Glu Ala Leu Val Glu Phe Glu Tyr Ala Leu Glu Asp Phe Leu
        195                 200                 205

Gly Asn Glu Phe Trp Arg Asn Trp Asp Gly Arg Leu Ser Lys Tyr Asp
            210                 215                 220

Ile Glu Thr His Arg Arg Cys Arg Gly Asn Gly Tyr Val Asp Leu Asp
225                 230                 235                 240

Ala Ser Val Met Gln Ser Asp Glu Tyr Val Leu Ser Gly Ala Tyr Asp
                245                 250                 255

Val Val Lys Met Gln Pro Pro Gly Thr Phe Asp Ser Pro Arg Tyr Tyr
            260                 265                 270

Leu His Leu Met Asp Gly Ile Tyr Val Asp Leu Ala Glu Val Thr Ala
        275                 280                 285

Tyr Arg Ser Tyr Gly Met Val Ile Gly Phe Trp Thr Asp Ser Lys Ser
            290                 295                 300

Pro Gln Leu Pro Thr Asp Phe Thr Arg Phe Asn Arg His Asn Cys Pro
305                 310                 315                 320

Val Gln Thr Val Ile Val Ile Pro Ser Leu
                325                 330

<210> SEQ ID NO 12
<211> LENGTH: 129
<212> TYPE: PRT
<213> ORGANISM: Bacteriophage f2

<400> SEQUENCE: 12

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
                20                  25                  30

Ile Ser Ser Asn Ser Arg Ser Gln Ala Tyr Lys Val Thr Cys Ser Val
            35                  40                  45

Arg Gln Ser Ser Ala Gln Asn Arg Lys Tyr Thr Ile Lys Val Glu Val
```

```
                50                  55                  60
Pro Lys Val Ala Thr Gln Thr Val Gly Gly Val Glu Leu Pro Val Ala
 65                  70                  75                  80

Ala Trp Arg Ser Tyr Leu Asn Leu Glu Leu Thr Ile Pro Ile Phe Ala
                     85                  90                  95

Thr Asn Ser Asp Cys Glu Leu Ile Val Lys Ala Met Gln Gly Leu Leu
                100                 105                 110

Lys Asp Gly Asn Pro Ile Pro Ser Ala Ile Ala Ala Asn Ser Gly Ile
            115                 120                 125

Tyr

<210> SEQ ID NO 13
<211> LENGTH: 128
<212> TYPE: PRT
<213> ORGANISM: Bacteriophage PP7

<400> SEQUENCE: 13

Met Ser Lys Thr Ile Val Leu Ser Val Gly Glu Ala Thr Arg Thr Leu
 1               5                  10                  15

Thr Glu Ile Gln Ser Thr Ala Asp Arg Gln Ile Phe Glu Glu Lys Val
                20                  25                  30

Gly Pro Leu Val Gly Arg Leu Arg Leu Thr Ala Ser Leu Arg Gln Asn
            35                  40                  45

Gly Ala Lys Thr Ala Tyr Arg Val Asn Leu Lys Leu Asp Gln Ala Asp
        50                  55                  60

Val Val Asp Cys Ser Thr Ser Val Cys Gly Glu Leu Pro Lys Val Arg
 65                  70                  75                  80

Tyr Thr Gln Val Trp Ser His Asp Val Thr Ile Val Ala Asn Ser Thr
                     85                  90                  95

Glu Ala Ser Arg Lys Ser Leu Tyr Asp Leu Thr Lys Ser Leu Val Ala
                100                 105                 110

Thr Ser Gln Val Glu Asp Leu Val Val Asn Leu Val Pro Leu Gly Arg
            115                 120                 125

<210> SEQ ID NO 14
<211> LENGTH: 131
<212> TYPE: PRT
<213> ORGANISM: bacteriophage AP205

<400> SEQUENCE: 14

Met Ala Asn Lys Pro Met Gln Pro Ile Thr Ser Thr Ala Asn Lys Ile
 1               5                  10                  15

Val Trp Ser Asp Pro Thr Arg Leu Ser Thr Thr Phe Ser Ala Ser Leu
                20                  25                  30

Leu Arg Gln Arg Val Lys Val Gly Ile Ala Glu Leu Asn Asn Val Ser
            35                  40                  45

Gly Gln Tyr Val Ser Val Tyr Lys Arg Pro Ala Pro Lys Pro Glu Gly
        50                  55                  60

Cys Ala Asp Ala Cys Val Ile Met Pro Asn Glu Asn Gln Ser Ile Arg
 65                  70                  75                  80

Thr Val Ile Ser Gly Ser Ala Glu Asn Leu Ala Thr Leu Lys Ala Glu
                     85                  90                  95

Trp Glu Thr His Lys Arg Asn Val Asp Thr Leu Phe Ala Ser Gly Asn
                100                 105                 110

Ala Gly Leu Gly Phe Leu Asp Pro Thr Ala Ala Ile Val Ser Ser Asp
            115                 120                 125
```

Thr Thr Ala
    130

<210> SEQ ID NO 15
<211> LENGTH: 132
<212> TYPE: PRT
<213> ORGANISM: Artificial Sequence
<220> FEATURE:
<223> OTHER INFORMATION: Bacteriophage Qbeta 240 mutant--chemically
      synthesized

<400> SEQUENCE: 15

Ala Lys Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 16
<211> LENGTH: 132
<212> TYPE: PRT
<213> ORGANISM: Artificial Sequence
<220> FEATURE:
<223> OTHER INFORMATION: Bacteriophage Q-beta 243 mutant--chemically
      synthesized

<400> SEQUENCE: 16

Ala Lys Leu Glu Thr Val Thr Leu Gly Lys Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 17
<211> LENGTH: 132
<212> TYPE: PRT
<213> ORGANISM: Artificial Sequence
<220> FEATURE:
<223> OTHER INFORMATION: Bacteriophage Q-beta 250 mutant--chemically synthesized

<400> SEQUENCE: 17

```
Ala Arg Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130
```

<210> SEQ ID NO 18
<211> LENGTH: 132
<212> TYPE: PRT
<213> ORGANISM: Artificial Sequence
<220> FEATURE:
<223> OTHER INFORMATION: Bacteriophage Q-beta 251 mutant--chemically synthesized

<400> SEQUENCE: 18

```
Ala Lys Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130
```

<210> SEQ ID NO 19

<211> LENGTH: 132
<212> TYPE: PRT
<213> ORGANISM: Artificial Sequence
<220> FEATURE:
<223> OTHER INFORMATION: Bacteriophage Q-beta 259 mutant--chemically synthesized

<400> SEQUENCE: 19

Ala Arg Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 20
<211> LENGTH: 185
<212> TYPE: PRT
<213> ORGANISM: Hepatitis B virus

<400> SEQUENCE: 20

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Ser Gln Ser Pro Arg Arg Arg
                165                 170                 175

Arg Ser Gln Ser Arg Glu Ser Gln Cys
            180                 185

<210> SEQ ID NO 21
<211> LENGTH: 188
<212> TYPE: PRT
<213> ORGANISM: Hepatitis B virus

<400> SEQUENCE: 21

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Gly Gly
65                  70                  75                  80

Lys Gly Gly Ser Arg Asp Leu Val Val Ser Tyr Val Asn Thr Asn Val
                85                  90                  95

Gly Leu Lys Phe Arg Gln Leu Leu Trp Phe His Ile Ser Cys Leu Thr
            100                 105                 110

Phe Gly Arg Glu Thr Val Leu Glu Tyr Leu Val Ser Phe Gly Val Trp
        115                 120                 125

Ile Arg Thr Pro Pro Ala Tyr Arg Pro Pro Asn Ala Pro Ile Leu Ser
    130                 135                 140

Thr Leu Pro Glu Thr Thr Val Val Arg Arg Asp Arg Gly Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Ser Arg Glu Ser Gln Cys
            180                 185

<210> SEQ ID NO 22
<211> LENGTH: 70
<212> TYPE: PRT
<213> ORGANISM: Felis domesticus

<400> SEQUENCE: 22

Glu Ile Cys Pro Ala Val Lys Arg Asp Val Asp Leu Phe Leu Thr Gly
1               5                   10                  15

Thr Pro Asp Glu Tyr Val Glu Gln Val Ala Gln Tyr Lys Ala Leu Pro
            20                  25                  30

Val Val Leu Glu Asn Ala Arg Ile Leu Lys Asn Cys Val Asp Ala Lys
        35                  40                  45

Met Thr Glu Glu Asp Lys Glu Asn Ala Leu Ser Leu Leu Asp Lys Ile
    50                  55                  60

Tyr Thr Ser Pro Leu Cys
65                  70

<210> SEQ ID NO 23
<211> LENGTH: 92
<212> TYPE: PRT
<213> ORGANISM: Felis domesticus

<400> SEQUENCE: 23

Val Lys Met Ala Glu Thr Cys Pro Ile Phe Tyr Asp Val Phe Phe Ala
1               5                   10                  15

```
Val Ala Asn Gly Asn Glu Leu Leu Asp Leu Ser Leu Thr Lys Val
                20                  25                  30

Asn Ala Thr Glu Pro Glu Arg Thr Ala Met Lys Lys Ile Gln Asp Cys
             35                  40                  45

Tyr Val Glu Asn Gly Leu Ile Ser Arg Val Leu Asp Gly Leu Val Met
         50                  55                  60

Thr Thr Ile Ser Ser Ser Lys Asp Cys Met Gly Glu Ala Val Gln Asn
 65                  70                  75                  80

Thr Val Glu Asp Leu Lys Leu Asn Thr Leu Gly Arg
                 85                  90

<210> SEQ ID NO 24
<211> LENGTH: 162
<212> TYPE: PRT
<213> ORGANISM: Artificial Sequence
<220> FEATURE:
<223> OTHER INFORMATION: fusion of chain 2+ chain 1--chemically
      synthesized

<400> SEQUENCE: 24

Val Lys Met Ala Glu Thr Cys Pro Ile Phe Tyr Asp Val Phe Phe Ala
 1               5                  10                  15

Val Ala Asn Gly Asn Glu Leu Leu Asp Leu Ser Leu Thr Lys Val
                20                  25                  30

Asn Ala Thr Glu Pro Glu Arg Thr Ala Met Lys Lys Ile Gln Asp Cys
             35                  40                  45

Tyr Val Glu Asn Gly Leu Ile Ser Arg Val Leu Asp Gly Leu Val Met
         50                  55                  60

Thr Thr Ile Ser Ser Ser Lys Asp Cys Met Gly Glu Ala Val Gln Asn
 65                  70                  75                  80

Thr Val Glu Asp Leu Lys Leu Asn Thr Leu Gly Arg Glu Ile Cys Pro
                 85                  90                  95

Ala Val Lys Arg Asp Val Asp Leu Phe Leu Thr Gly Thr Pro Asp Glu
                100                 105                 110

Tyr Val Glu Gln Val Ala Gln Tyr Lys Ala Leu Pro Val Val Leu Glu
            115                 120                 125

Asn Ala Arg Ile Leu Lys Asn Cys Val Asp Ala Lys Met Thr Glu Glu
        130                 135                 140

Asp Lys Glu Asn Ala Leu Ser Leu Leu Asp Lys Ile Tyr Thr Ser Pro
145                 150                 155                 160

Leu Cys

<210> SEQ ID NO 25
<211> LENGTH: 90
<212> TYPE: PRT
<213> ORGANISM: Felis domesticus

<400> SEQUENCE: 25

Val Lys Met Ala Glu Thr Cys Pro Ile Phe Tyr Asp Val Phe Phe Ala
 1               5                  10                  15

Val Ala Asn Gly Asn Glu Leu Leu Asp Leu Ser Leu Thr Lys Val
                20                  25                  30

Asn Ala Thr Glu Pro Glu Arg Thr Ala Met Lys Lys Ile Gln Asp Cys
             35                  40                  45

Tyr Val Glu Asn Gly Leu Ile Ser Arg Val Leu Asp Gly Leu Val Met
         50                  55                  60

Ile Ala Ile Asn Glu Tyr Cys Met Gly Glu Ala Val Gln Asn Thr Val
```

```
                    65                  70                  75                  80
Glu Asp Leu Lys Leu Asn Thr Leu Gly Arg
                85                  90

<210> SEQ ID NO 26
<211> LENGTH: 78
<212> TYPE: PRT
<213> ORGANISM: Felis domesticus

<400> SEQUENCE: 26

Val Lys Met Ala Glu Thr Cys Pro Ile Phe Tyr Asp Val Phe Phe Ala
1               5                   10                  15

Val Ala Asn Gly Asn Glu Leu Leu Asp Leu Ser Leu Thr Lys Val
                20                  25                  30

Asn Ala Thr Glu Pro Glu Arg Thr Ala Met Lys Lys Ile Gln Asp Cys
            35                  40                  45

Tyr Val Glu Asn Gly Leu Ile Ser Arg Val Leu Asp Gly Leu Val Met
        50                  55                  60

Pro Ser Thr Asn Ile Ala Trp Val Lys Gln Phe Arg Thr Pro
65                  70                  75

<210> SEQ ID NO 27
<211> LENGTH: 27
<212> TYPE: PRT
<213> ORGANISM: Felis domesticus

<400> SEQUENCE: 27

Lys Arg Asp Val Asp Leu Phe Leu Thr Gly Thr Pro Asp Glu Tyr Val
1               5                   10                  15

Glu Gln Val Ala Gln Tyr Lys Ala Leu Pro Val
                20                  25

<210> SEQ ID NO 28
<211> LENGTH: 27
<212> TYPE: PRT
<213> ORGANISM: Felis domesticus

<400> SEQUENCE: 28

Lys Ala Leu Pro Val Val Leu Glu Asn Ala Arg Ile Leu Lys Asn Cys
1               5                   10                  15

Val Asp Ala Lys Met Thr Glu Asp Lys Glu
                20                  25

<210> SEQ ID NO 29
<211> LENGTH: 26
<212> TYPE: PRT
<213> ORGANISM: Felis domesticus

<400> SEQUENCE: 29

Phe Phe Ala Val Ala Asn Gly Asn Glu Leu Leu Asp Leu Ser Leu
1               5                   10                  15

Thr Lys Val Asn Ala Thr Glu Pro Glu Arg
                20                  25

<210> SEQ ID NO 30
<211> LENGTH: 19
<212> TYPE: PRT
<213> ORGANISM: Felis domesticus

<400> SEQUENCE: 30

Glu Glu Asp Lys Glu Asn Ala Leu Ser Leu Leu Asp Lys Ile Tyr Thr
```

-continued

```
                 1               5              10              15

Ser Pro Leu

<210> SEQ ID NO 31
<211> LENGTH: 19
<212> TYPE: PRT
<213> ORGANISM: Felis domesticus

<400> SEQUENCE: 31

Met Gly Glu Ala Val Gln Asn Thr Val Glu Asp Leu Lys Leu Asn Thr
1               5                  10                  15

Leu Gly Arg

<210> SEQ ID NO 32
<211> LENGTH: 16
<212> TYPE: PRT
<213> ORGANISM: Felis domesticus

<400> SEQUENCE: 32

Glu Glu Asp Lys Glu Asn Ala Leu Ser Leu Leu Asp Lys Ile Tyr Thr
1               5                  10                  15

<210> SEQ ID NO 33
<211> LENGTH: 174
<212> TYPE: PRT
<213> ORGANISM: Artificial Sequence
<220> FEATURE:
<223> OTHER INFORMATION: fusion with his tag and GGC--chemically
      synthesized

<400> SEQUENCE: 33

Met Val Lys Met Ala Glu Thr Cys Pro Ile Phe Tyr Asp Val Phe Phe
1               5                  10                  15

Ala Val Ala Asn Gly Asn Glu Leu Leu Leu Asp Leu Ser Leu Thr Lys
            20                  25                  30

Val Asn Ala Thr Glu Pro Glu Arg Thr Ala Met Lys Lys Ile Gln Asp
        35                  40                  45

Cys Tyr Val Glu Asn Gly Leu Ile Ser Arg Val Leu Asp Gly Leu Val
    50                  55                  60

Met Thr Thr Ile Ser Ser Ser Lys Asp Cys Met Gly Glu Ala Val Gln
65                  70                  75                  80

Asn Thr Val Glu Asp Leu Lys Leu Asn Thr Leu Gly Arg Glu Ile Cys
                85                  90                  95

Pro Ala Val Lys Arg Asp Val Asp Leu Phe Leu Thr Gly Thr Pro Asp
            100                 105                 110

Glu Tyr Val Glu Gln Val Ala Gln Tyr Lys Ala Leu Pro Val Val Leu
        115                 120                 125

Glu Asn Ala Arg Ile Leu Lys Asn Cys Val Asp Ala Lys Met Thr Glu
    130                 135                 140

Glu Asp Lys Glu Asn Ala Leu Ser Leu Leu Asp Lys Ile Tyr Thr Ser
145                 150                 155                 160

Pro Leu Cys Leu Glu His His His His His Gly Gly Cys
                165                 170

<210> SEQ ID NO 34
<211> LENGTH: 85
<212> TYPE: DNA
<213> ORGANISM: Artificial Sequence
<220> FEATURE:
<223> OTHER INFORMATION: primer 1F--chemically synthesized
```

<400> SEQUENCE: 34
gtacatatgg aaatctgccc ggctgttaaa cgtgacgttg acctgttcct gaccggtacc    60
ccggacgaat acgttgaaca ggttg    85

<210> SEQ ID NO 35
<211> LENGTH: 38
<212> TYPE: DNA
<213> ORGANISM: Artificial Sequence
<220> FEATURE:
<223> OTHER INFORMATION: primer 2R--chemically synthesized

<400> SEQUENCE: 35
ggcagagctt tgtactgagc aacctgttca acgtattc    38

<210> SEQ ID NO 36
<211> LENGTH: 75
<212> TYPE: DNA
<213> ORGANISM: Artificial Sequence
<220> FEATURE:
<223> OTHER INFORMATION: primer 3F--chemically synthesized

<400> SEQUENCE: 36
gctcagtaca aagctctgcc ggttgttctg gaaaacgctc gtatcctgaa aaactgcgtt    60
gacgctaaaa tgacc    75

<210> SEQ ID NO 37
<211> LENGTH: 89
<212> TYPE: DNA
<213> ORGANISM: Artificial Sequence
<220> FEATURE:
<223> OTHER INFORMATION: primer 4R--chemically synthesized

<400> SEQUENCE: 37
cctctcgagg cacagcgggg aggtgtagat tttgtccagc agggacagag cgttttcttt    60
gtcttcttcg gtcattttag cgtcaacgc    89

<210> SEQ ID NO 38
<211> LENGTH: 76
<212> TYPE: DNA
<213> ORGANISM: Artificial Sequence
<220> FEATURE:
<223> OTHER INFORMATION: primer 5F--chemically synthesized

<400> SEQUENCE: 38
gtacatatgg ttaaaatggc tgaaacctgc ccgatcttct acgacgtttt cttcgctgtt    60
gctaacggta acgaac    76

<210> SEQ ID NO 39
<211> LENGTH: 75
<212> TYPE: DNA
<213> ORGANISM: Artificial Sequence
<220> FEATURE:
<223> OTHER INFORMATION: primer 6R--chemically synthesized

<400> SEQUENCE: 39
ggtacgttcc ggttcggtag cgttaacttt ggtcagggac aggtccagca gcagttcgtt    60
accgttagca acagc    75

<210> SEQ ID NO 40
<211> LENGTH: 80
<212> TYPE: DNA

<213> ORGANISM: Artificial Sequence
<220> FEATURE:
<223> OTHER INFORMATION: primer 7F--chemically synthesized

<400> SEQUENCE: 40

```
ctaccgaacc ggaacgtacc gctatgaaaa aaatccagga ctgctacgtt gaaaacggtc    60
tgatctcccg tgttctggac                                                80
```

<210> SEQ ID NO 41
<211> LENGTH: 71
<212> TYPE: DNA
<213> ORGANISM: Artificial Sequence
<220> FEATURE:
<223> OTHER INFORMATION: primer 8R--chemically synthesized

<400> SEQUENCE: 41

```
gcttcaccca tgcagtcttt ggaggaggag atggtggtca taaccagacc gtccagaaca    60
cgggagatca g                                                         71
```

<210> SEQ ID NO 42
<211> LENGTH: 75
<212> TYPE: DNA
<213> ORGANISM: Artificial Sequence
<220> FEATURE:
<223> OTHER INFORMATION: primer 9F--chemically synthesized

<400> SEQUENCE: 42

```
caaagactgc atgggtgaag ctgttcagaa caccgttgaa gacctgaaac tgaacaccct    60
gggtcgctcg agagg                                                     75
```

<210> SEQ ID NO 43
<211> LENGTH: 21
<212> TYPE: DNA
<213> ORGANISM: Artificial Sequence
<220> FEATURE:
<223> OTHER INFORMATION: primer 10R--chemically synthesized

<400> SEQUENCE: 43

```
cctctcgagc gacccagggt g                                              21
```

<210> SEQ ID NO 44
<211> LENGTH: 45
<212> TYPE: DNA
<213> ORGANISM: Artificial Sequence
<220> FEATURE:
<223> OTHER INFORMATION: primer linker--chemically synthesized

<400> SEQUENCE: 44

```
cgtttaacag ccgggcagat ttcacgaccc aggtgttca gtttc                     45
```

<210> SEQ ID NO 45
<211> LENGTH: 28
<212> TYPE: DNA
<213> ORGANISM: Artificial Sequence
<220> FEATURE:
<223> OTHER INFORMATION: primer 12-1--chemically synthesized

<400> SEQUENCE: 45

```
gtacatatgg aaatctgccc ggctgtta                                       28
```

<210> SEQ ID NO 46
<211> LENGTH: 48
<212> TYPE: DNA
<213> ORGANISM: Artificial Sequence

```
<220> FEATURE:
<223> OTHER INFORMATION: primer 12-3--chemically synthesized

<400> SEQUENCE: 46
gcaggtttca gccattttaa cgcacagcgg ggaggtgtag attttgtc        48

<210> SEQ ID NO 47
<211> LENGTH: 39
<212> TYPE: DNA
<213> ORGANISM: Artificial Sequence
<220> FEATURE:
<223> OTHER INFORMATION: primer 12-2-1--chemically synthesized

<400> SEQUENCE: 47
cctctcgaga cgacccaggg tgttcagttt caggtcttc                  39

<210> SEQ ID NO 48
<211> LENGTH: 58
<212> TYPE: DNA
<213> ORGANISM: Artificial Sequence
<220> FEATURE:
<223> OTHER INFORMATION: primer 1-10aa--chemically synthesized

<400> SEQUENCE: 48
ggtggaggag gtagcggtgg aggaggtagc gaaatctgcc cggctgttaa acgtgacg    58

<210> SEQ ID NO 49
<211> LENGTH: 41
<212> TYPE: DNA
<213> ORGANISM: Artificial Sequence
<220> FEATURE:
<223> OTHER INFORMATION: primer 2-5aa--chemically synthesized

<400> SEQUENCE: 49
gctacctcct ccaccacgac ccagggtgtt cagtttcagg t               41

<210> SEQ ID NO 50
<211> LENGTH: 43
<212> TYPE: DNA
<213> ORGANISM: Artificial Sequence
<220> FEATURE:
<223> OTHER INFORMATION: primer 1-5aa--chemically synthesized

<400> SEQUENCE: 50
ggtggaggag gtagcgaaat ctgcccggct gttaaacgtg acg             43

<210> SEQ ID NO 51
<211> LENGTH: 59
<212> TYPE: DNA
<213> ORGANISM: Artificial Sequence
<220> FEATURE:
<223> OTHER INFORMATION: primer 2-10aa--chemically synthesized

<400> SEQUENCE: 51
ggtggaggag gtagcggtgg aggaggtagc gttaaaatgg ctgaaacctg cccgatctt   59

<210> SEQ ID NO 52
<211> LENGTH: 42
<212> TYPE: DNA
<213> ORGANISM: Artificial Sequence
<220> FEATURE:
<223> OTHER INFORMATION: primer 1-5aa--chemically synthesized

<400> SEQUENCE: 52
gctacctcct ccaccgcaca gcggggaggt gtagattttg tc              42
```

<210> SEQ ID NO 53
<211> LENGTH: 44
<212> TYPE: DNA
<213> ORGANISM: Artificial Sequence
<220> FEATURE:
<223> OTHER INFORMATION: primer 2-5aa--chemically synthesized

<400> SEQUENCE: 53
ggtggaggag gtagcgttaa aatggctgaa acctgcccga tctt                       44

<210> SEQ ID NO 54
<211> LENGTH: 175
<212> TYPE: PRT
<213> ORGANISM: Artificial Sequence
<220> FEATURE:
<223> OTHER INFORMATION: FELD1-10aa--chemically synthesized

<400> SEQUENCE: 54

Met Val Lys Met Ala Glu Thr Cys Pro Ile Phe Tyr Asp Val Phe Phe
1               5                   10                  15

Ala Val Ala Asn Gly Asn Glu Leu Leu Leu Asp Leu Ser Leu Thr Lys
            20                  25                  30

Val Asn Ala Thr Glu Pro Glu Arg Thr Ala Met Lys Lys Ile Gln Asp
        35                  40                  45

Cys Tyr Val Glu Asn Gly Leu Ile Ser Arg Val Leu Asp Gly Leu Val
    50                  55                  60

Met Thr Thr Ile Ser Ser Ser Lys Asp Cys Met Gly Glu Ala Val Gln
65                  70                  75                  80

Asn Thr Val Glu Asp Leu Lys Leu Asn Thr Leu Gly Arg Gly Gly Gly
                85                  90                  95

Gly Ser Gly Gly Gly Gly Ser Glu Ile Cys Pro Ala Val Lys Arg Asp
            100                 105                 110

Val Asp Leu Phe Leu Thr Gly Thr Pro Asp Glu Tyr Val Glu Gln Val
        115                 120                 125

Ala Gln Tyr Lys Ala Leu Pro Val Val Leu Glu Asn Ala Arg Ile Leu
    130                 135                 140

Lys Asn Cys Val Asp Ala Lys Met Thr Glu Glu Asp Lys Glu Asn Ala
145                 150                 155                 160

Leu Ser Leu Leu Asp Lys Ile Tyr Thr Ser Pro Leu Cys Leu Glu
                165                 170                 175

<210> SEQ ID NO 55
<211> LENGTH: 180
<212> TYPE: PRT
<213> ORGANISM: Artificial Sequence
<220> FEATURE:
<223> OTHER INFORMATION: FELD1-15aa--chemically synthesized

<400> SEQUENCE: 55

Met Val Lys Met Ala Glu Thr Cys Pro Ile Phe Tyr Asp Val Phe Phe
1               5                   10                  15

Ala Val Ala Asn Gly Asn Glu Leu Leu Leu Asp Leu Ser Leu Thr Lys
            20                  25                  30

Val Asn Ala Thr Glu Pro Glu Arg Thr Ala Met Lys Lys Ile Gln Asp
        35                  40                  45

Cys Tyr Val Glu Asn Gly Leu Ile Ser Arg Val Leu Asp Gly Leu Val
    50                  55                  60

Met Thr Thr Ile Ser Ser Ser Lys Asp Cys Met Gly Glu Ala Val Gln
65                  70                  75                  80

```
Asn Thr Val Glu Asp Leu Lys Leu Asn Thr Leu Gly Arg Gly Gly
                85                  90                  95

Gly Ser Gly Gly Gly Ser Gly Gly Gly Ser Glu Ile Cys Pro
            100                 105                 110

Ala Val Lys Arg Asp Val Asp Leu Phe Leu Thr Gly Thr Pro Asp Glu
            115                 120                 125

Tyr Val Glu Gln Val Ala Gln Tyr Lys Ala Leu Pro Val Val Leu Glu
            130                 135                 140

Asn Ala Arg Ile Leu Lys Asn Cys Val Asp Ala Lys Met Thr Glu Glu
145                 150                 155                 160

Asp Lys Glu Asn Ala Leu Ser Leu Leu Asp Lys Ile Tyr Thr Ser Pro
                165                 170                 175

Leu Cys Leu Glu
            180

<210> SEQ ID NO 56
<211> LENGTH: 165
<212> TYPE: PRT
<213> ORGANISM: Artificial Sequence
<220> FEATURE:
<223> OTHER INFORMATION: FD12--chemically synthesized

<400> SEQUENCE: 56

Met Glu Ile Cys Pro Ala Val Lys Arg Asp Val Asp Leu Phe Leu Thr
1               5                   10                  15

Gly Thr Pro Asp Glu Tyr Val Glu Gln Val Ala Gln Tyr Lys Ala Leu
            20                  25                  30

Pro Val Val Leu Glu Asn Ala Arg Ile Leu Lys Asn Cys Val Asp Ala
        35                  40                  45

Lys Met Thr Glu Glu Asp Lys Glu Asn Ala Leu Ser Leu Leu Asp Lys
    50                  55                  60

Ile Tyr Thr Ser Pro Leu Cys Val Lys Met Ala Glu Thr Cys Pro Ile
65                  70                  75                  80

Phe Tyr Asp Val Phe Phe Ala Val Ala Asn Gly Asn Glu Leu Leu Leu
                85                  90                  95

Asp Leu Ser Leu Thr Lys Val Asn Ala Thr Glu Pro Glu Arg Thr Ala
            100                 105                 110

Met Lys Lys Ile Gln Asp Cys Tyr Val Glu Asn Gly Leu Ile Ser Arg
        115                 120                 125

Val Leu Asp Gly Leu Val Met Thr Thr Ile Ser Ser Lys Asp Cys
    130                 135                 140

Met Gly Glu Ala Val Gln Asn Thr Val Glu Asp Leu Lys Leu Asn Thr
145                 150                 155                 160

Leu Gly Arg Leu Glu
                165

<210> SEQ ID NO 57
<211> LENGTH: 180
<212> TYPE: PRT
<213> ORGANISM: Artificial Sequence
<220> FEATURE:
<223> OTHER INFORMATION: FD12-15aa--chemically synthesized

<400> SEQUENCE: 57

Met Glu Ile Cys Pro Ala Val Lys Arg Asp Val Asp Leu Phe Leu Thr
1               5                   10                  15

Gly Thr Pro Asp Glu Tyr Val Glu Gln Val Ala Gln Tyr Lys Ala Leu
```

```
                20                  25                  30
Pro Val Val Leu Glu Asn Ala Arg Ile Leu Lys Asn Cys Val Asp Ala
            35                  40                  45
Lys Met Thr Glu Glu Asp Lys Glu Asn Ala Leu Ser Leu Leu Asp Lys
        50                  55                  60
Ile Tyr Thr Ser Pro Leu Cys Gly Gly Gly Ser Gly Gly Gly Gly
65                  70                  75                  80
Ser Gly Gly Gly Gly Ser Val Lys Met Ala Glu Thr Cys Pro Ile Phe
                85                  90                  95
Tyr Asp Val Phe Phe Ala Val Ala Asn Gly Asn Glu Leu Leu Leu Asp
            100                 105                 110
Leu Ser Leu Thr Lys Val Asn Ala Thr Glu Pro Glu Arg Thr Ala Met
        115                 120                 125
Lys Lys Ile Gln Asp Cys Tyr Val Glu Asn Gly Leu Ile Ser Arg Val
        130                 135                 140
Leu Asp Gly Leu Val Met Thr Thr Ile Ser Ser Ser Lys Asp Cys Met
145                 150                 155                 160
Gly Glu Ala Val Gln Asn Thr Val Glu Asp Leu Lys Leu Asn Thr Leu
                165                 170                 175
Gly Arg Leu Glu
            180

<210> SEQ ID NO 58
<211> LENGTH: 10
<212> TYPE: PRT
<213> ORGANISM: Artificial Sequence
<220> FEATURE:
<223> OTHER INFORMATION: gamma linker 1--chemically synthesized

<400> SEQUENCE: 58

Cys Gly Asp Lys Thr His Thr Ser Pro Pro
1               5                   10

<210> SEQ ID NO 59
<211> LENGTH: 6
<212> TYPE: PRT
<213> ORGANISM: Artificial Sequence
<220> FEATURE:
<223> OTHER INFORMATION: N terminial glycine linker--chemically
      synthesized

<400> SEQUENCE: 59

Gly Cys Gly Gly Gly Gly
1               5

<210> SEQ ID NO 60
<211> LENGTH: 6
<212> TYPE: PRT
<213> ORGANISM: Artificial Sequence
<220> FEATURE:
<223> OTHER INFORMATION: N-terminal glycine serine linker--chemically
      synthesized

<400> SEQUENCE: 60

Cys Gly Gly Gly Gly Ser
1               5

<210> SEQ ID NO 61
<211> LENGTH: 9
<212> TYPE: PRT
<213> ORGANISM: Artificial Sequence
<220> FEATURE:
```

```
<223> OTHER INFORMATION: GCGSGGGGS linker--chemically synthesized

<400> SEQUENCE: 61

Gly Cys Gly Ser Gly Gly Gly Gly Ser
1               5

<210> SEQ ID NO 62
<211> LENGTH: 10
<212> TYPE: PRT
<213> ORGANISM: Artificial Sequence
<220> FEATURE:
<223> OTHER INFORMATION: C-terminal gamma 1 linker--chemically
      synthesized

<400> SEQUENCE: 62

Asp Lys Thr His Thr Ser Pro Pro Cys Gly
1               5                   10

<210> SEQ ID NO 63
<211> LENGTH: 18
<212> TYPE: PRT
<213> ORGANISM: Artificial Sequence
<220> FEATURE:
<223> OTHER INFORMATION: C terminal gamma linker 3--chemically
      synthesized

<400> SEQUENCE: 63

Pro Lys Pro Ser Thr Pro Pro Gly Ser Ser Gly Gly Ala Pro Gly Gly
1               5                   10                  15

Cys Gly

<210> SEQ ID NO 64
<211> LENGTH: 6
<212> TYPE: PRT
<213> ORGANISM: Artificial Sequence
<220> FEATURE:
<223> OTHER INFORMATION: C terminal glycine linker--chemically
      synthesized

<400> SEQUENCE: 64

Gly Gly Gly Gly Cys Gly
1               5

<210> SEQ ID NO 65
<211> LENGTH: 6
<212> TYPE: PRT
<213> ORGANISM: Artificial Sequence
<220> FEATURE:
<223> OTHER INFORMATION: C terminal glycine serine linker--chemically
      synthesized

<400> SEQUENCE: 65

Ser Gly Gly Gly Gly Cys
1               5

<210> SEQ ID NO 66
<211> LENGTH: 10
<212> TYPE: PRT
<213> ORGANISM: Artificial Sequence
<220> FEATURE:
<223> OTHER INFORMATION: GSGGGGSGCG linker--chemically synthesized

<400> SEQUENCE: 66

Gly Ser Gly Gly Gly Gly Ser Gly Cys Gly
1               5                   10
```

```
<210> SEQ ID NO 67
<211> LENGTH: 6
<212> TYPE: PRT
<213> ORGANISM: Artificial Sequence
<220> FEATURE:
<223> OTHER INFORMATION: glycine lysine linker--chemically synthesized

<400> SEQUENCE: 67

Gly Gly Lys Lys Gly Cys
1               5

<210> SEQ ID NO 68
<211> LENGTH: 6
<212> TYPE: PRT
<213> ORGANISM: Artificial Sequence
<220> FEATURE:
<223> OTHER INFORMATION: glycine lysine linker 2--chemically synthesized

<400> SEQUENCE: 68

Cys Gly Lys Lys Gly Gly
1               5

<210> SEQ ID NO 69
<211> LENGTH: 17
<212> TYPE: PRT
<213> ORGANISM: Artificial Sequence
<220> FEATURE:
<223> OTHER INFORMATION: CGGPKPSTPPGSSGGAP--chemically synthesized

<400> SEQUENCE: 69

Cys Gly Gly Pro Lys Pro Ser Thr Pro Pro Gly Ser Ser Gly Gly Ala
1               5                   10                  15

Pro
```